United States Patent
Jensen et al.

(10) Patent No.: US 8,906,936 B2
(45) Date of Patent: *Dec. 9, 2014

(54) PHARMACEUTICAL COMBINATION COMPRISING CO-ADMINISTRATION OF TAXANE AND N-(1-CYCLOHEXYL-2-{2-[4-(4-FLUORO-BENZOYL)-THIAZOL-2-YL]-PYRROLIDIN-1-YL}-2-OXO-ETHYL)-2-METHYLAMINO-PROPIONAMIDE OR PHARMACEUTICALLY ACCEPTABLE SALT(S) THEREOF

(71) Applicant: Novartis AG, Basel (CH)

(72) Inventors: Michael Rugaard Jensen, Basel (CH); Christopher Sean Straub, Stow, MA (US); Leigh Zawel, Hingham, MA (US); Mary Ann Tran, Somerville, MA (US); Youzhen Wang, Newton, MA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/761,634

(22) Filed: Feb. 7, 2013

(65) Prior Publication Data
US 2013/0217719 A1    Aug. 22, 2013

Related U.S. Application Data

(63) Continuation of application No. 12/862,979, filed on Aug. 25, 2010, now abandoned, which is a continuation of application No. 12/158,130, filed as application No. PCT/US2006/048163 on Dec. 18, 2006, now abandoned.

(60) Provisional application No. 60/752,146, filed on Dec. 20, 2005.

(51) Int. Cl.
| | | |
|---|---|---|
| *A01N 43/42* | (2006.01) | |
| *A61K 31/44* | (2006.01) | |
| *A61K 31/16* | (2006.01) | |
| *A61K 31/425* | (2006.01) | |
| *A61K 45/06* | (2006.01) | |
| *A61K 31/437* | (2006.01) | |
| *A61K 31/475* | (2006.01) | |
| *C07D 471/04* | (2006.01) | |
| *A61K 31/337* | (2006.01) | |

(52) U.S. Cl.
CPC .............. *A61K 31/437* (2013.01); *A61K 31/16* (2013.01); *A61K 31/425* (2013.01); *A61K 45/06* (2013.01); *A61K 31/475* (2013.01); *C07D 471/04* (2013.01); *A61K 31/337* (2013.01)
USPC .......................................................... 514/300

(58) Field of Classification Search
None
See application file for complete search history.

(56) References Cited

U.S. PATENT DOCUMENTS 5,565,478 A    10/1996   Kohn et al.

FOREIGN PATENT DOCUMENTS

| WO | WO 02/16402 | 2/2002 |
|---|---|---|
| WO | 2004005248 | 1/2004 |
| WO | 2005069888 | 8/2005 |
| WO | WO 2005/069894 | 8/2005 |
| WO | WO 2005/094818 | 10/2005 |
| WO | WO 2005/097791 | 10/2005 |
| WO | 2007075525 A2 | 7/2007 |
| WO | 2008057172 A2 | 5/2008 |

OTHER PUBLICATIONS

Williams et al. (Foye's Principles of Medicinal Chemistry, 5th edition, pp. 50 and 59-61, 2002).*
Arnt et al., "Synthetic Smac/DIABLO Peptides Enhance the Effects of Chemotherapeutic Agents by Binding XIAP and ciAP1 in Situ", Journal of Biological Chemistry, vol. 277 (46), pp. 44236-44243, 2002.
Sun et al., "Structure-based Design, Synthesis and Biochemical Testing of Novel and Potent Smac Peptido-mimetics". Bioorganic & Medicinal Chemistry Letters: vol. 15(3) pp. 793-797, 2005.
Patani et al., (Chem Rev., 1996, 96, 3146-76).
Berenbaum et al., What is synergy? Pharmacological Reviews, 1989.

* cited by examiner

*Primary Examiner* — Anna Pagonakis
(74) *Attorney, Agent, or Firm* — Jennifer Chapman

(57) ABSTRACT

The invention provides a pharmaceutical combination comprising:
  a) compounds that inhibit the binding of the Smac protein to IAPs; and
  b) a taxane,
and a method for treating or preventing a proliferative disease using such a combination.

6 Claims, 26 Drawing Sheets

PHARMACEUTICAL COMBINATION COMPRISING CO-ADMINISTRATION OF TAXANE AND N-(1-CYCLOHEXYL-2-{2-[4-(4-FLUORO-BENZOYL)-THIAZOL-2-YL]-PYRROLIDIN-1-YL}-2-OXO-ETHYL)-2-METHYLAMINO-PROPIONAMIDE OR PHARMACEUTICALLY ACCEPTABLE SALT(S) THEREOF

This application is a continuation of application Ser. No. 12/862,979 filed on Aug. 25, 2010, which is a continuation of application Ser. No. 12/158,130, filed on Jun. 19, 2008, which is a National Stage of International Application No. PCT/US2006/048163 filed on Dec. 18, 2006, which claims benefit of U.S. provisional Application No. 60/752,146 filed on Dec. 20, 2005, the entire disclosures of which are hereby incorporated by reference.

The present invention relates to a pharmaceutical combination comprising compounds that inhibit the binding of the Smac protein to Inhibitor of Apoptosis Proteins (IAPs) and a taxane, and the uses of such a combination, e.g., in proliferative diseases, e.g., tumors, myelomas and leukemias.

In spite of numerous treatment options for patients with proliferative diseases, there remains a need for effective and safe molecularly targeted anti-proliferative agents. Combination of such exploratory agents with existing therapies sometimes results in a synergistic interaction and enhanced therapeutic benefit relative to either agent alone.

SUMMARY OF THE INVENTION

It has now been found that a combination comprising at least one compound that inhibits the binding of the Smac protein to IAPs and a taxane, e.g., as defined below, has a beneficial effect on proliferative diseases, e.g., tumors, myelomas and leukemias.

DETAILED DESCRIPTION OF THE INVENTION

Figure 1:
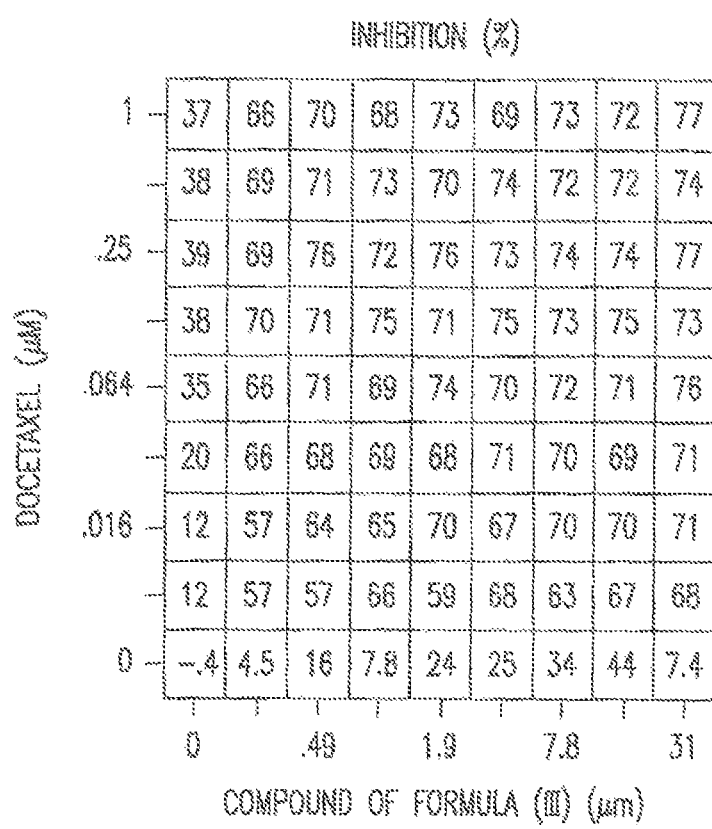
FIG. 1 indicates anti-proliferative activity of compound of formula (III) alone (bottom row), Docetaxel alone (most leftward column) and combinations of the two agents across a dose range in Example 1

The invention relates to a pharmaceutical combination which comprises:
(a) a taxane; and
(b) a compound (IAP inhibitor) that inhibits the caspase-9 inhibiting properties of an IAP; and, optionally,
(c) at least one pharmaceutically acceptable carrier for simultaneous, separate or sequential use, in particular, for the treatment of a proliferative disease, especially a solid tumor disease; a pharmaceutical composition comprising such a combination; the use of such a combination for the preparation of a medicament for the treatment of a proliferative disease; a commercial package or product comprising such a combination as a combined preparation for simultaneous, separate or sequential use; and to a method of treatment of a warm-blooded animal, especially a human. A greater than additive effect is seen when compounds (a) and (b) are used in combination.

Taxanes are microtubule targeting agents that bind to tubulin and block cell division by interfering with the function of the mitotic spindle. Taxanes represent a first-line treatment option for metastatic breast, lung, ovarian and digestive cancers and are commonly used in the adjuvant setting for breast cancer.

Taxanes include Paclitaxel, marketed as TAXOL and docetaxel, marketed as TAXOTERE. Other taxanes include vinorelbine and the epothilones, such as epothilone B and patupilone.

Compounds that inhibit the binding of the Smac protein to IAPs include compounds of the formula (I):

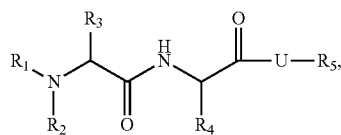

wherein
$R_1$ is H, $C_1$-$C_4$alkyl, $C_1$-$C_4$alkenyl, $C_1$-$C_4$alkynyl or $C_3$-$C_{10}$cycloalkyl, which are unsubstituted or substituted;
$R_2$ is H, $C_1$-$C_4$alkyl, $C_1$-$C_4$alkenyl, $C_1$-$C_4$alkynyl or $C_3$-$C_{10}$cycloalkyl, which are unsubstituted or substituted;
$R_3$ is H, —$CF_3$, $C_1$-$C_4$alkyl, $C_1$-$C_4$alkenyl, $C_1$-$C_4$alkynyl, wherein Z is H, —OH, F, Cl, —$CH_3$, —$CF_3$, —$CH_2F$ or —$CH_2OH$, or
$R_2$ and $R_3$, together with the nitrogen, form a het ring;
$R_4$ is $C_1$-$C_{16}$straight- or branched-alkyl, $C_1$-$C_{16}$alkenyl, $C_1$-$C_{16}$alkynyl or —$C_3$-$C_{10}$cycloalkyl, —$(CH_2)_{1-6}Z_1$, —$(CH_2)_{0-6}$aryl and —$(CH_2)_{0-6}$het, wherein alkyl, cycloalkyl and phenyl are unsubstituted or substituted, wherein
$Z_1$ is —$N(R_8)$—C(O)—$C_1$-$C_{10}$alkyl, —$N(R_8)$—C(O)—$(CH_2)_{1-6}C_3$-$C_7$cycloalkyl, —$N(R_8)$—C(O)—$(CH_2)_{0-6}$phenyl, —$N(R_8)$—C(O)—$(CH_2)_{1-6}$het, —C(O)—N($R_9$)($R_{10}$), —C(O)—O—$C_1$-$C_{10}$alkyl, —C(O)—O—$(CH_2)_{1-6}C_3$-$C_7$cycloalkyl, —C(O)—O—$(CH_2)_{0-6}$phenyl, —C(O)—O—$(CH_2)_{1-6}$het, —O—C(O)$C_1$-$C_{10}$alkyl, —O—C(O)—$(CH_2)_{1-6}C_3$-$C_7$cycloalkyl, —O—C(O)—$(CH_2)_{0-6}$phenyl, —O—C(O)—$(CH_2)_{1-6}$het, wherein alkyl, cycloalkyl and phenyl are unsubstituted or substituted; and het is a 5- to 7-membered heterocyclic ring containing 1-4 heteroatoms selected from N, O and S, or an 8- to 12-membered fused ring system including at least one 5- to 7-membered heterocyclic ring containing 1, 2 or 3 heteroatoms selected from N, O, and S, which heterocyclic ring or fused ring system is unsubstituted or substituted on a carbon or nitrogen atom,
wherein
$R_8$ is H, —$CH_3$, —$CF_3$, —$CH_2OH$ or —$CH_2Cl$;
$R_9$ and $R_{10}$ are each independently H, $C_1$-$C_4$alkyl, $C_3$-$C_7$cycloalkyl, —$(CH_2)_{1-6}C_3$-$C_7$cycloalkyl, —$(CH_2)_{0-6}$phenyl, wherein alkyl, cycloalkyl and phenyl are unsubstituted or substituted, or
$R_9$ and $R_{10}$, together with the nitrogen, form het;
$R_5$ is H, $C_1$-$C_{10}$alkyl, aryl, phenyl, $C_3$-$C_7$cycloalkyl, —$(CH_2)_{1-6}C_3$-$C_7$cycloalkyl, —$C_1$-$C_{10}$alkyl-aryl, —$(CH_2)_{0-6}C_3$-$C_7$cycloalkyl-$(CH_2)_{0-6}$phenyl, —$(CH_2)_{0-4}CH$—(($CH_2)_{1-4}$phenyl)$_2$, —$(CH_2)_{0-6}CH$(phenyl)$_2$, -indanyl, —C(O)—$C_1$-$C_{10}$alkyl, —C(O)—$(CH_2)_{1-6}C_3$-$C_7$cycloalkyl, —C(O)—$(CH_2)_{0-6}$phenyl, —$(CH_2)_{0-6}$C(O)-phenyl, —$(CH_2)_{0-6}$het, —C(O)—$(CH_2)_{1-6}$het, or
$R_5$ is a residue of an amino acid, wherein the alkyl, cycloalkyl, phenyl and aryl substituents are unsubstituted or substituted; and
U is as shown in formula (II):

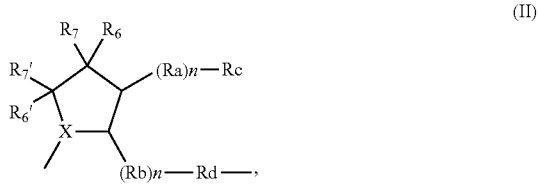

wherein
n is 0-5;
X is —CH or N;
Ra and Rb are independently an O, S or N atom or $C_0$-$C_8$alkyl, wherein one or more of the carbon atoms in the alkyl chain may be replaced by a heteroatom selected from O, S or N, and where the alkyl may be unsubstituted or substituted;
Rd is selected from:
(a) -Re-Q-(Rf)$_p$(Rg)$_q$; or
(b) Ar$_1$-D-Ar$_2$,
wherein
p and q are independently 0 or 1;
Re is $C_1$-$C_8$alkyl or alkylidene and
Re which may be unsubstituted or substituted;
Q is N, O, S, S(O), or S(O)$_2$;
Ar$_1$ and Ar$_2$ are substituted or unsubstituted aryl or het;
Rf and Rg are each independently H, —$C_1$-$C_{10}$alkyl, $C_1$-$C_{10}$alkylaryl, —OH, —O—$C_1$-$C_{10}$alkyl, —$(CH_2)_{0-6}C_3$-$C_7$cycloalkyl, —O—$(CH_2)_{0-6}$aryl, phenyl, aryl, phenyl-phenyl, —$(CH_2)_{1-6}$het, —O—$(CH_2)_{1-6}$het, —OR$_{11}$, —C(O)—R$_{11}$, —C(O)—N(R$_{11}$)(R$_{12}$), —N(R$_{11}$)(R$_{12}$), —S—R$_{11}$, —S(O)—R$_{11}$, —S(O)$_2$—R$_{11}$, —S(O)$_2$—NR$_{11}$—S(O)$_2$—R$_{12}$, S—$C_1$-$C_{10}$alkyl, aryl-$C_1$-$C_4$alkyl, het-$C_1$-$C_4$alkyl, wherein alkyl, cycloalkyl, het and aryl are unsubstituted or substituted, —$SO_2$—$C_1$-$C_2$alkyl, —$SO_2$—$C_1$-$C_2$alkylphenyl, —O—$C_1$-$C_4$alkyl, or Rg and Rf form a ring selected from het or aryl;

D is —CO—, —C(O)—$C_1$-$C_7$alkylene or arylene, —$CF_2$—, —O—, —S(O)$_r$, where r is 0-2, 1,3-dioxolane or $C_1$-$C_7$alkyl-OH, where alkyl, alkylene or arylene may be unsubstituted or substituted with one or more halogens, OH, —O—$C_1$-$C_6$alkyl, —S—$C_1$-$C_6$alkyl or —$CF_3$, or D is —N(Rh), wherein Rh is H, $C_1$-$C_7$alkyl (unsubstituted or substituted), aryl, —O($C_1$-$C_7$cycloalkyl) (unsubstituted or substituted), C(O)—$C_1$-$C_{10}$alkyl, C(O)—$C_0$-$C_{10}$alkyl-aryl, C—O—$C_1$-$C_{10}$alkyl, C—O—$C_0$-$C_{10}$alkyl-aryl or $SO_2$—$C_1$-$C_{10}$-alkyl, $SO_2$—($C_0$-$C_{10}$-alkylaryl);

Rc is H, or

Rc and Rd may together form a cycloalkyl or het, where if Rd and Rc form a cycloalkyl or het, $R_5$ is attached to the formed ring at a C or N atom;

$R_6$, $R_7$, $R'_6$ and $R'_7$ are each independently H, —$C_1$-$C_{10}$alkyl, —$C_1$-$C_{10}$alkoxy, aryl-$C_1$-$C_{10}$alkoxy, —OH, —O—$C_1$-$C_{10}$alkyl, —$(CH_2)_{0-6}C_3$-$C_7$cycloalkyl, —O—$(CH_2)_{0-6}$aryl, phenyl, —$(CH_2)_{1-6}$het, —O—$(CH_2)_{1-6}$het, —$OR_{11}$, —C(O)—$R_{11}$, —C(O)—N($R_{11}$)($R_{12}$), —N($R_{11}$)($R_{12}$), —S—$R_{11}$, —S(O)—$R_{11}$, —S(O)$_2$—$R_{11}$, —S(O)$_2$—$NR_{11}R_{12}$, —$NR_{11}$—S(O)$_2$—$R_{12}$, wherein alkyl, cycloalkyl and aryl are unsubstituted or substituted; and $R_6$, $R_7$, $R'_6$ and $R'_7$ can be united to form a ring system, wherein $R_{11}$ and $R_{12}$ are independently H, $C_1$-$C_{10}$alkyl, —$(CH_2)_{0-6}C_3$-$C_7$cycloalkyl, —$(CH_2)_{0-6}$(CH)$_{0-1}$(aryl)$_{1-2}$, —C(O)—$C_1$-$C_{10}$alkyl, —C(O)—$(CH_2)_{1-6}C_3$-$C_7$cycloalkyl, —C(O)—O—$(CH_2)_{0-6}$aryl, —C(O)—$(CH_2)_{0-6}$O-fluorenyl, —C(O)—NH—$(CH_2)_{0-6}$aryl, —C(O)—$(CH_2)_{0-6}$aryl, —C(O)—$(CH_2)_{1-6}$het, —C(S)—$C_1$-$C_{10}$alkyl, —C(S)—$(CH_2)_{1-6}C_3$-$C_7$cycloalkyl, —C(S)—O—$(CH_2)_{0-6}$aryl, —C(S)—$(CH_2)_{0-6}$O-fluorenyl, —C(S)—NH—$(CH_2)_{0-6}$aryl, —C(S)—$(CH_2)_{0-6}$aryl, —C(S)—$(CH_2)_{1-6}$het, wherein alkyl, cycloalkyl and aryl are unsubstituted or substituted, or $R_{11}$ and $R_{12}$ are a substituent that facilitates transport of the molecule across a cell membrane, or $R_{11}$ and $R_{12}$, together with the nitrogen atom, form het, wherein the alkyl substituents of $R_{11}$ and $R_{12}$ may be unsubstituted or substituted by one or more substituents selected from $C_1$-$C_{10}$alkyl, halogen, OH, —O—$C_1$-$C_6$alkyl, —S—$C_1$-$C_6$alkyl or —$CF_3$;

substituted cycloalkyl substituents of $R_{11}$ and $R_{12}$ are substituted by one or more substituents selected from a $C_1$-$C_{10}$alkene, $C_1$-$C_6$alkyl, halogen, OH, —O—$C_1$-$C_6$alkyl, —S—$C_1$-$C_6$alkyl or —$CF_3$; and substituted phenyl or aryl of $R_{11}$ and $R_{12}$ are substituted by one or more substituents selected from halogen, hydroxy, $C_1$-$C_4$alkyl, $C_1$-$C_4$alkoxy, nitro, —CN, —O—C(O)—$C_1$-$C_4$alkyl and —C(O)—O—$C_1$-$C_4$aryl;

or pharmaceutically acceptable salts thereof.

The general terms used hereinbefore and hereinafter preferably have within the context of this disclosure the following meanings, unless otherwise indicated:

"Aryl" is an aromatic radical having 6-14 carbon atoms, which may be fused or unfused, and which is unsubstituted or substituted by 1 or more, preferably 1 or 2 substituents, wherein the substituents are as described below. Preferred "aryl" is phenyl, naphthyl or indanyl.

"Het" refers to heteroaryl and heterocyclic rings and fused rings containing aromatic and non-aromatic heterocyclic rings. "Het" is a 5- to 7-membered heterocyclic ring containing 1-4 heteroatoms selected from N, O and S, or an 8- to 12-membered fused ring system including at least one 5- to 7-membered heterocyclic ring containing 1, 2 or 3 heteroatoms selected from N, O and S. Suitable het substituents include unsubstituted and substituted pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, 1,4-oxathiapane, furyl, thienyl, pyrrole, pyrazole, triazole, 1,2,3-triazole, tetrazolyl, oxadiazole, thiophene, imidazol, pyrrolidine, pyrrolidone, thiazole, oxazole, pyridine, pyrimidine, isoxazolyl, pyrazine, quinoline, isoquinoline, pyridopyrazine, pyrrolopyridine, furopyridine, indole, benzofuran, benzothiofuran, benzindole, benzoxazole, pyrroloquinoline and the like. The het substituents are unsubstituted or substituted on a carbon atom by halogen, especially fluorine or chlorine; hydroxy; $C_1$-$C_4$alkyl, such as methyl and ethyl; $C_1$-$C_4$alkoxy, especially methoxy and ethoxy; nitro; —O—C(O)—$C_1$-$C_4$alkyl or —C(O)—O—$C_1$-$C_4$alkyl or on a nitrogen by $C_1$-$C_4$alkyl, especially methyl or ethyl; —O—C(O)—$C_1$-$C_4$alkyl or —C(O)—O—$C_1$-$C_4$alkyl, such as carbomethoxy or carboethoxy.

When two substituents together with a commonly bound nitrogen are het, it is understood that the resulting heterocyclic ring is a nitrogen-containing ring, such as aziridine, azetidine, azole, piperidine, piperazine, morphiline, pyrrole, pyrazole, thiazole, oxazole, pyridine, pyrimidine, isoxazolyl and the like.

Halogen is fluorine, chlorine, bromine or iodine, especially fluorine and chlorine.

Unless otherwise specified "alkyl" includes straight- or branched-chain alkyl, such as methyl, ethyl, n-propyl, isopropyl, n-butyl, sec-butyl, tert-butyl, n-pentyl and branched pentyl, n-hexyl and branched hexyl and the like.

A "cycloalkyl" group means $C_3$-$C_{10}$cycloalkyl having 3- to 8-ring carbon atoms and may be, e.g., cyclopropyl, cyclobutyl, cyclopentyl, cyclohexyl, cycloheptyl or cyclooctyl. Preferably, cycloalkyl is cycloheptyl. The cycloalkyl group may be unsubstituted or substituted with any of the substituents defined below, preferably halo, hydroxy or $C_1$-$C_4$alkyl, such as methyl.

The amino acid residues include a residue of a standard amino acid, such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The amino acid residues also include the side chains of uncommon and modified amino acids. Uncommon and modified amino acids are known to those of skill in the art [see, e.g., Fields, Tiam and Barany, Synthetic Peptides A Users Guide, University of Wisconsin Biochemistry Center, Chapter 3, (1992)] and include amino acids, such as 4-hydroxyproline, 5-hydroxylysine, desmosine, beta (β)-alanine, alpha (α)-, gamma (γ)- and β-aminobutric acid, homocysteine, homoserine, citrulline, ornithine, 2- or 3-amino adipic acid, 6-aminocaproic acid, 2- or 3-aminoisobutric acid, 2,3-diaminopropionic acid, diphenylalanine, hydroxyproline and the like. If the side chain of the amino acid residue contains a derivatizable group, such as COOH, —OH or amino, the side chain may be derivatized by a substituent that reacts with the derivatizable group. For example, acidic amino acids, like aspartic and glutamic acid, or hydroxy substituted side chains, like those of serine or threonine, may be derivatized to form an ester, or amino side chains may form amide or alkylamino derivatives. In particular, the derivative may be a substituent that facilitates transport across a cell membrane. In addition, any carboxylic acid group in the amino acid residue, e.g., an α-carboxylic acid group, may be derivatized as discussed above to form an ester or amide.

Substituents that facilitate transport of the molecule across a cell membrane are known to those of skill in the medicinal chemistry arts. See, e.g., Gangewar et al., *Drug Dis Today*, Vol. 2, pp. 148-155 (1997); and Bundgaard and Moss, *Pharma Res, Vol.* 7, p. 885 (1990). Generally, such substituents are lipophillic substituents. Such lipophillic substituents include a $C_6$-$C_{30}$alkyl, which is saturated, monounsaturated, polyunsaturated, including methylene-interrupted polyene, phenyl, phenyl which substituted by one or two $C_1$-$C_8$alkyl groups, $C_5$-$C_9$cycloalkyl, $C_5$-$C_9$cycloalkyl, which is substituted by one or two $C_1$-$C_8$alkyl groups, —$X_1$-phenyl, —$X_1$-phenyl, which is substituted in the phenyl ring by one or two $C_1$-$C_8$alkyl groups, $X_1$-$C_5$-$C_9$cycloalkyl or $X_1$-$C_5$-$C_9$cycloalkyl, which is substituted by one or two $C_1$-$C_8$alkyl groups, where $X_1$ is $C_1$-$C_{24}$alkyl, which is saturated, monounsaturated or poly-unsaturated and straight- or branched-chain.

Unsubstituted is intended to mean that hydrogen is the only substituent.

Any of the above defined aryl, het, alkyl, cycloalkyl, or heterocyclic groups may be unsubstituted or independently substituted by up to 4, preferably 1, 2 or 3 substituents, selected from the group consisting of: halo, such as Cl or Br; hydroxy; lower alkyl, such as $C_1$-$C_3$lower alkyl; lower alkyl, which may be substituted with any of the substituents defined herein; lower alkenyl; lower alkynyl; lower alkanoyl; alkoxy, such as methoxy, aryl, such as phenyl or benzyl; substituted aryl, such as fluoro phenyl or methoxy phenyl; amino; mono- or di-substituted amino; amino lower alkyl, such as dimethylamino; acetyl amino; amino lower alkoxy, such as ethoxyamine; nitro; cyano; cyano lower alkyl; carboxy; esterified carboxy, such as lower alkoxy carbonyl, e.g., methoxy carbonyl; n-propoxy carbonyl or iso-propoxy carbonyl; alkanoyl; benzoyl; carbamoyl; N-mono- or N,N-di-substituted carbamoyl; carbamates; alkyl carbamic acid esters; amidino; guanidine; urea; ureido; mercapto; sulfo; lower alkylthio; sulfoamino; sulfonamide; benzosulfonamide; sulfonate; sulfanyl lower alkyl, such as methyl sulfanyl; sulfoamino; substituted or unsubstituted sulfonamide, such as benzo sulfonamide; substituted or unsubstituted sulfonate, such as chloro-phenyl sulfonate; lower alkylsulfinyl; phenylsulfinyl; phenyl-lower alkylsulfinyl; alkylphenylsulfinyl; lower alkanesulfonyl; phenylsulfonyl; phenyl-lower alkylsulfonyl; alkylphenylsulfonyl; halogen-lower alkylmercapto; halogen-lower alkylsulfonyl, such as especially trifluoromethane sulfonyl; phosphono (—P(=O)(OH)$_2$); hydroxy-lower alkoxy phosphoryl or di-lower alkoxyphosphoryl; substituted urea, such as 3-trifluoro-methyl-phenyl urea; alkyl carbamic acid ester or carbamates, such as ethyl-N-phenyl-carbamate or —NR$_4$R$_5$, wherein R$_4$ and R$_5$ can be the same or different and are independently H; lower alkyl, e.g., methyl, ethyl or propyl, or R$_4$ and R$_5$, together with the N atom, form a 3- to 8-membered heterocyclic ring containing 1-4 nitrogen, oxygen or sulfur atoms, e.g., piperazinyl, pyrazinyl, lower alkyl-piperazinyl, pyridyl, indolyl, thiophenyl, thiazolyl, n-methyl piperazinyl, benzothiophenyl, pyrrolidinyl, piperidino or imidazolinyl, where the heterocyclic ring may be substituted with any of the substituents defined herein.

Preferably, the above-mentioned alkyl, cycloalkyl, aryl or het groups may be substituted by halogen, carbonyl, thiol, S(O), S(O$_2$), —OH, —SH, —OCH$_3$, —SCH$_3$, —CN, —SCN or nitro.

Where the plural form is used for compounds, salts, pharmaceutical preparations, diseases and the like, this is intended to mean also a single compound, salt or the like.

It will be apparent to one of skill in the art when a compound of the invention can exist as a salt form, especially as an acid addition salt or a base addition salt. When a compound can exist in a salt form, such salt forms are included within the scope of the invention. Although any salt form may be useful in chemical manipulations, such as purification procedures, only pharmaceutically acceptable salts are useful for pharmaceutically products.

Pharmaceutically acceptable salts include, when appropriate, pharmaceutically acceptable base addition salts and acid addition salts, e.g., metal salts, such as alkali and alkaline earth metal salts; ammonium salts; organic amine addition salts; amino acid addition salts; and sulfonate salts. Acid addition salts include inorganic acid addition, salts such as hydrochloride, sulfate and phosphate; and organic acid addition salts, such as alkyl sulfonate, arylsulfonate, acetate, maleate, fumarate, tartrate, citrate and lactate. Examples of metal salts are alkali metal salts, such as lithium salt, sodium salt and potassium salt; alkaline earth metal salts, such as magnesium salt and calcium salt, aluminum salt and zinc salt. Examples of ammonium salts are ammonium salt and tetramethylammonium salt. Examples of organic amine addition salts are salts with morpholine and piperidine. Examples of amino acid addition salts are salts with glycine, phenylalanine, glutamic acid and lysine. Sulfonate salts include mesylate, tosylate and benzene sulfonic acid salts.

In view of the close relationship between the compounds in free form and those in the form of their salts, including those salts that can be used as intermediates, e.g., in the purification or identification of the compounds, tautomers or tautomeric mixtures and their salts, any reference to the compounds hereinbefore and hereinafter especially the compounds of the formula (I), is to be understood as referring also to the corresponding tautomers of these compounds, especially of compounds of the formula (I), tautomeric mixtures of these compounds, especially of compounds of the formula (I), or salts of any of these, as appropriate and expedient and if not mentioned otherwise.

Any asymmetric carbon atom may be present in the (R)-, (S)- or (R,S)-configuration, preferably in the (R)- or (S)-configuration. Substituents at a ring at atoms with saturated bonds may, if possible, be present in cis (=Z-) or trans (=E-) form. The compounds may thus be present as mixtures of isomers or preferably as pure isomers, preferably as enantiomer-pure diastereomers or pure enantiomers.

Compounds within the scope of formula (I) and the process for their manufacture are disclosed in WO 05/097791 published on Oct. 20, 2005, which is hereby incorporated into the present application by reference. A preferred compounds within the scope of formula (I) is N-[1-cyclohexyl-2-oxo-2-(6-phenethyl-octahydro-pyrrolo[2,3-c]pyridin-1-yl-ethyl]-2-methylamino-propionamide of formula (III):

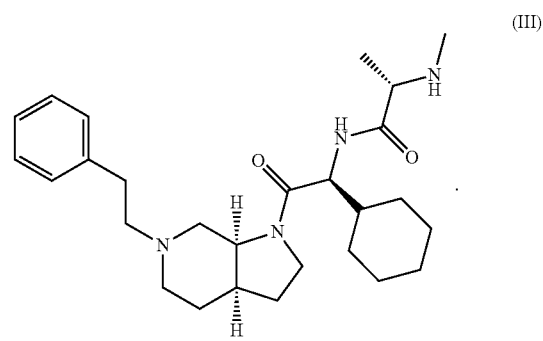 [SMILES: CN[C@@H](C)C(=O)N[C@H](C(=O)N1CC[C@H]2CCN(CCc3ccccc3)C[C@H]21)C1CCCCC1]

Additional compounds that inhibit the binding of the Smac protein to IAPs include compounds of the formula (IV):

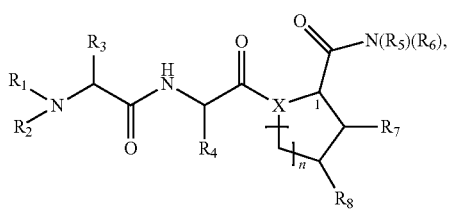

(IV)

wherein
$R_1$ is H;
$R_2$ is H, $C_1$-$C_4$alkyl, which is unsubstituted or substituted by one or more substituents selected from halogen, —OH, —SH, —OCH$_3$, —SCH$_3$, —CN, —SCN and nitro;
$R_3$ is H, —CF$_3$, —C$_2$F$_5$, —CH$_2$—Z, wherein Z is H, —OH, F, Cl, —CH$_3$, —CF$_3$, —CH$_2$Cl, —CH$_2$F or —CH$_2$OH, or
$R_2$ and $R_3$, together with the nitrogen, form a $C_3$-$C_6$heteroaliphatic ring;
$R_4$ is $C_1$-$C_{16}$straight-chain alkyl, $C_3$-$C_{10}$branched-chain alkyl, —(CH$_2$)$_{0-6}$C$_3$-C$_7$cycloalkyl, —(CH$_2$)$_{1-6}$Z$_1$, —(CH$_2$)$_{0-6}$phenyl and —(CH$_2$)$_{0-6}$het, wherein the alkyl, cycloalkyl and phenyl substituents are unsubstituted or substituted,
wherein
$Z_1$ is —N(R$_9$)—C(O)—C$_1$-C$_{10}$alkyl, —N(R$_9$)—C(O)—(CH$_2$)$_{1-6}$C$_3$-C$_7$cycloalkyl, —N(R$_9$)—C(O)—(CH$_2$)$_{0-6}$phenyl, —N(R$_9$)—C(O)—(CH$_2$)$_{1-6}$het, —C(O)—N(R$_{10}$)(R$_{11}$), —C(O)—O—C$_1$-C$_{10}$alkyl, —C(O)—O—(CH$_2$)$_{1-6}$C$_3$-C$_7$cycloalkyl, —C(O)—O—(CH$_2$)$_{0-6}$phenyl, —C(O)—O—(CH$_2$)$_{1-6}$het, —O—C(O)—C$_1$-C$_{10}$alkyl, —O—C(O)—(CH$_2$)$_{1-6}$C$_3$-C$_7$cycloalkyl, —O—C(O)—(CH$_2$)$_{0-6}$phenyl, —O—C(O)—(CH$_2$)$_{1-6}$het, wherein the alkyl, cycloalkyl and phenyl substituents are unsubstituted or substituted,
wherein
$R_9$ is H, —CH$_3$, —CF$_3$, —CH$_2$OH or CH$_2$Cl;
$R_{10}$ and $R_{11}$ are each independently H, $C_1$-$C_4$alkyl, $C_3$-$C_7$cycloalkyl, —(CH$_2$)$_{1-6}$C$_3$-C$_7$cycloalkyl, —(CH$_2$)$_{0-6}$phenyl, wherein the alkyl, cycloalkyl and phenyl substituents are unsubstituted or substituted, or
$R_{10}$ and $R_{11}$, together with the nitrogen, are het;
het is a 5- to 7-membered heterocyclic ring containing 1, 2 or 3 heteroatoms selected from N, O and S, or an 8- to 12-membered fused ring system including at least one 5- to 7-membered heterocyclic ring containing 1, 2 or 3 heteroatoms selected from N, O and S, which heterocyclic ring or fused ring system is unsubstituted or substituted on a carbon atom by halogen, hydroxy, $C_1$-$C_4$alkyl, $C_1$-$C_4$alkoxy, nitro, —O—C(O)—C$_1$-$C_4$alkyl or —C(O)—O—C$_1$-$C_4$alkyl or on a nitrogen by $C_1$-$C_4$alkyl, —O—C(O)—C$_1$-$C_4$alkyl or —C(O)—O—C$_1$-$C_4$alkyl;
X is CH or N;
$R_5$ is H, $C_1$-$C_{10}$alkyl, $C_3$-$C_7$cycloalkyl, —(CH$_2$)$_{1-6}$C$_3$-C$_7$cycloalkyl, —C$_1$-C$_{10}$alkyl-aryl, —(CH$_2$)$_{0-6}$C$_3$-C$_7$cycloalkyl-(CH$_2$)$_{0-6}$phenyl, —(CH$_2$)$_{0-4}$—CH—((CH$_2$)$_{1-4}$phenyl)$_2$, —(CH$_2$)$_{0-6}$CH(phenyl)$_2$, —C(O)—C$_1$-C$_{10}$alkyl, —C(O)—(CH$_2$)$_{1-6}$C$_3$-C$_7$cycloalkyl, —C(O)—(CH$_2$)$_{0-6}$phenyl, —(CH$_2$)$_{1-6}$het, —C(O)—(CH$_2$)$_{1-6}$het, or
$R_5$ is a residue of an amino acid, wherein the alkyl, cycloalkyl, phenyl and aryl substituents are unsubstituted or substituted;
$R_6$ is H, methyl, ethyl, —CF$_3$, —CH$_2$OH or —CH$_2$Cl, or
$R_5$ and $R_6$, together with the nitrogen, are het;
$R_7$ and $R_8$ are cis relative to the acyl substituent at the one position of the ring and are each independently H, —C$_1$-C$_{10}$alkyl, —OH, —O—C$_1$-C$_{10}$alkyl, —(CH$_2$)$_{0-6}$C$_3$-C$_7$cycloalkyl, —O—(CH$_2$)$_{0-6}$aryl, phenyl, —(CH$_2$)$_{1-6}$het, —O—(CH$_2$)$_{1-6}$het, —N(R$_{12}$)(R$_{13}$), —S—R$_{12}$, —S(O)—R$_{12}$, —S(O)$_2$—R$_{12}$, —S(O)$_2$—NR$_{12}$R$_{13}$, wherein the alkyl, cycloalkyl and aryl substituents are unsubstituted or substituted,
wherein
$R_{12}$ and $R_{13}$ are independently H, $C_1$-$C_{10}$alkyl, —(CH$_2$)$_{0-6}$C$_3$-C$_7$cycloalkyl, —(CH$_2$)$_{0-6}$(CH)$_{0-1}$(aryl)$_{1-2}$, —C(O)—C$_1$-C$_{10}$alkyl, —C(O)—(CH$_2$)$_{1-6}$C$_3$-C$_7$cycloalkyl, —C(O)—O—(CH$_2$)$_{0-6}$aryl, —C(O)—(CH$_2$)$_{0-6}$O-fluorenyl, —C(O)—NH—(CH$_2$)$_{0-6}$aryl, —C(O)—(CH$_2$)$_{0-6}$aryl, —C(O)—(CH$_2$)$_{1-6}$het, wherein the alkyl, cycloalkyl and aryl substituents are unsubstituted or substituted; or a substituent that facilitates transport of the molecule across a cell membrane, or
$R_{12}$ and $R_{13}$, together with the nitrogen, are het; and
aryl is phenyl or naphthyl which is unsubstituted or substituted;
n is 0, 1 or 2;
substituted alkyl substituents are substituted by one or more substituents selected from a double bond, halogen, OH, —O—C$_1$-$C_6$alkyl, —S—C$_1$-$C_6$alkyl and —CF$_3$;
substituted cycloalkyl substituents are substituted by one or more substituents selected from a double bond, $C_1$-$C_6$alkyl, halogen, OH, —O—C$_1$-$C_6$alkyl, —S—C$_1$-$C_6$alkyl and —CF$_3$; and
substituted phenyl or aryl are substituted by one or more substituents selected from halogen, hydroxy, $C_1$-$C_4$alkyl, $C_1$-$C_4$alkoxy, nitro, —CN, —O—C(O)—C$_1$-$C_4$alkyl and —C(O)—O—C$_1$-$C_4$alkyl.

Unsubstituted is intended to mean that hydrogen is the only substituent.

Halogen is fluorine, chlorine, bromine or iodine, especially fluorine and chlorine.

Unless otherwise specified alkyl substituents include straight- or branched-chain alkyl, such as methyl, ethyl, n-propyl, isopropyl, n-butyl, sec-butyl, tert-butyl, n-pentyl and branched pentyl, n-hexyl and branched hexyl and the like.

Cycloalkyl substituents include cyclopropyl, cyclobutyl, cyclopentyl, cyclohexyl and cycloheptyl.

Compounds within the scope of formula (VIII) and the process for their manufacture are disclosed in WO 04/005284, which is hereby incorporated into the present application by reference.

In each case where citations of patent applications are given above, the subject matter relating to the compounds is hereby incorporated into the present application by reference. Comprised are likewise the pharmaceutically acceptable salts thereof, the corresponding racemates, diastereoisomers, enantiomers, tautomers, as well as the corresponding crystal modifications of above disclosed compounds where present, e.g., solvates, hydrates and polymorphs, which are disclosed therein. The compounds used as active ingredients in the combinations of the invention can be prepared and administered as described in the cited documents, respectively. Also within the scope of this invention is the combination of more than two separate active ingredients as set forth above, i.e., a pharmaceutical combination within the scope of this invention could include three active ingredients or more.

In accordance with the particular findings of the present invention, there is provided:

1. A pharmaceutical combination comprising:
   a) a compound that inhibit the binding of the Smac protein to IAPs of formula (I) or (IV); and
   b) at least one taxane.

2. A method for treating or preventing proliferative disease in a subject in need thereof, comprising co-administration to said subject, e.g., concomitantly or in sequence, of a therapeutically effective amount of a compound that inhibit the binding of the Smac protein to IAPs of formula (I) or (VIII) and a taxane. Examples of proliferative diseases include, e.g., tumors, leukemias and myelomas.

3. A pharmaceutical combination as defined under 1) above, e.g. for use in a method as defined under 2) above.

4. A pharmaceutical combination as defined under 1) above for use in the preparation of a medicament for use in a method as defined under 2) above.

Utility of the combination of the invention in a method as hereinabove specified, may be demonstrated in animal test methods, as well as in clinic, e.g., in accordance with the methods hereinafter described.

It has now surprisingly been found that the combination of a compounds that inhibit the binding of the Smac protein to IAPs and a taxane possesses therapeutic properties, which render it particularly useful as a treatment for proliferative diseases.

In another embodiment, the instant invention provides a method for treating proliferative diseases comprising administering to a mammal in need of such treatment a therapeutically effective amount of the combination of compounds that inhibit the binding of the Smac protein to IAPs and a taxane or pharmaceutically acceptable salts or prodrugs thereof.

In another embodiment, compounds that inhibit the binding of the Smac protein to IAPs are selected from compounds of formulae (I) and (IV) as defined above.

Preferably, the instant invention provides a method for treating mammals, especially humans, suffering from proliferative diseases comprising administering to a mammal in need of such treatment an inhibiting amount of the combination of compounds that inhibit the binding of the Smac protein to IAPs and a taxane or pharmaceutically acceptable salts thereof.

In the present description, the term "treatment" includes both prophylactic or preventative treatment, as well as curative or disease suppressive treatment, including treatment of patients at risk of contracting the disease or suspected to have contracted the disease, as well as ill patients. This term further includes the treatment for the delay of progression of the disease.

The term "curative: as used herein, means efficacy in treating ongoing episodes involving proliferative diseases.

The term "prophylactic" means the prevention of the onset or recurrence of diseases involving proliferative diseases.

The term "delay of progression", as used herein, means administration of the active compound to patients being in a pre-stage or in an early phase of the disease to be treated, in which patients, e.g. a pre-form of the corresponding disease is diagnosed or which patients are in a condition, e.g., during a medical treatment or a condition resulting from an accident, under which it is likely that a corresponding disease will develop.

This unforeseeable range of properties means that the use of the combination of a compounds that inhibit the binding of the Smac protein to IAPs and taxanes are of particular interest for the manufacture of a medicament for the treatment of proliferative diseases.

To demonstrate that the combination of a compounds that inhibit the binding of the Smac protein to IAPs and taxanes is particularly suitable for the treatment of proliferative diseases with good therapeutic margin and other advantages, clinical trials can be carried out in a manner known to the skilled person.

A. Combined Treatment

A combination which comprises:
   (a) a taxane; and
   (b) an IAP inhibitor, in which the active ingredients are present in each case in free form or in the form of a pharmaceutically acceptable salt; and, optionally, at least one pharmaceutically acceptable carrier, will be referred to hereinafter as a COMBINATION OF THE INVENTION.

Suitable clinical studies are, e.g., open-label, dose escalation studies in patients with proliferative diseases. Such studies prove in particular the synergism of the active ingredients of the COMBINATION OF THE INVENTION. The beneficial effects can be determined directly through the results of these studies which are known as such to a person skilled in the art. Such studies are, in particular, suitable to compare the effects of a monotherapy using the active ingredients and a COMBINATION OF THE INVENTION. Preferably, the dose of:

agent (a) is escalated until the Maximum Tolerated Dosage is reached; and
   agent (b) is administered with a fixed dose.

Alternatively, the agent (a) is administered in a fixed dose and the dose of agent (b) is escalated. Each patient receives doses of the agent (a) either daily or intermittent. The efficacy of the treatment can be determined in such studies, e.g., after 12, 18 or 24 weeks by evaluation of symptom scores every 6 weeks.

The administration of a pharmaceutical COMBINATION OF THE INVENTION results not only in a beneficial effect, e.g., a synergistic therapeutic effect, e.g., with regard to alleviating, delaying progression of or inhibiting the symptoms, but also in further surprising beneficial effects, e.g., fewer side effects, an improved quality of life or a decreased morbidity, compared with a monotherapy applying only one of the pharmaceutically active ingredients used in the combination of the invention.

A further benefit is that lower doses of the active ingredients of the COMBINATION OF THE INVENTION can be used, e.g., that the dosages need not only often be smaller but are also applied less frequently, which may diminish the incidence or severity of side effects. This is in accordance with the desires and requirements of the patients to be treated.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

It is one objective of this invention to provide a pharmaceutical composition comprising a quantity, which is jointly therapeutically effective at targeting or preventing proliferative diseases a COMBINATION OF THE INVENTION. In this composition, agents (a) and (b) may be administered together, one after the other or separately in one combined unit dosage form or in two separate unit dosage forms. The unit dosage form may also be a fixed combination.

The pharmaceutical compositions for separate administration of agents (a) and (b) or for the administration in a fixed combination, i.e., a single galenical composition comprising at least two combination partners (a) and (b), according to the invention may be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g., as indicated above, or in combination with one or more pharmaceutically acceptable carriers or diluents, especially suitable for enteral or parenteral application.

Suitable pharmaceutical compositions contain, for example, from about 0.1% to about 99.9%, preferably from about 1% to about 60%, of the active ingredient(s). Pharmaceutical preparations for the combination therapy for enteral or parenteral administration are, e.g., those in unit dosage forms, such as sugar-coated tablets, tablets, capsules or suppositories, or ampoules. If not indicated otherwise, these are prepared in a manner known per se, e.g., by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In particular, a therapeutically effective amount of each of the combination partner of the combination of the invention may be administered simultaneously or sequentially and in any order, and the components may be administered separately or as a fixed combination. For example, the method of preventing or treating proliferative diseases according to the invention may comprise:
 (i) administration of the first agent (a) in free or pharmaceutically acceptable salt form; and
 (ii) administration of an agent (b) in free or pharmaceutically acceptable salt form,
simultaneously or sequentially in any order, in jointly therapeutically effective amounts, preferably in synergistically effective amounts, e.g., in daily or intermittently dosages corresponding to the amounts described herein. The individual combination partners of the combination of the invention may be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The term "a combined preparation", as used herein, defines especially a "kit of parts" in the sense that the combination partners (a) and (b) as defined above can be dosed independently or by use of different fixed combinations with distinguished amounts of the combination partners (a) and (b), i.e., simultaneously or at different time points. The parts of the kit of parts can then, e.g., be administered simultaneously or chronologically staggered, that is at different time points and with equal or different time intervals for any part of the kit of parts. The ratio of the total amounts of the combination partner (a) to the combination partner (b) to be administered in the combined preparation can be varied, e.g., in order to cope with the needs of a patient sub-population to be treated or the needs of the single.

The effective dosage of each of the combination partners employed in the combination of the invention may vary depending on the particular compound or pharmaceutical composition employed, the mode of administration, the condition being treated, the severity of the condition being treated. Thus, the dosage regimen of the combination of the invention is selected in accordance with a variety of factors including the route of administration and the renal and hepatic function of the patient. A clinician or physician of ordinary skill can readily determine and prescribe the effective amount of the single active ingredients required to alleviate, counter or arrest the progress of the condition. Optimal precision in achieving concentration of the active ingredients within the range that yields efficacy without toxicity requires a regimen based on the kinetics of the active ingredients' availability to target sites.

Daily dosages for agent (a) or (b) or will, of course, vary depending on a variety of factors, for example the compound chosen, the particular condition to be treated and the desired effect. In general, however, satisfactory results are achieved on administration of agent (a) at daily dosage rates of the order of ca. 0.03-5 mg/kg/day, particularly 0.1-5 mg/kg/day, e.g., 0.1-2.5 mg/kg/day, as a single dose or in divided doses. Agents (a) and (b) may be administered by any conventional route, in particular, enterally, e.g., orally, e.g., in the form of tablets, capsules, drink solutions or parenterally, e.g., in the form of injectable solutions or suspensions. Suitable unit dosage forms for oral administration comprise from ca. 0.02-50 mg active ingredient, usually 0.1-30 mg, e.g., agent (a) or (b), together with one or more pharmaceutically acceptable diluents or carriers therefore.

Agent (b) may be administered to a human in a daily dosage range of 0.5-1000 mg. Suitable unit dosage forms for oral administration comprise from ca. 0.1-500 mg active ingredient, together with one or more pharmaceutically acceptable diluents or carriers therefore.

The administration of a pharmaceutical combination of the invention results not only in a beneficial effect, e.g., a synergistic therapeutic effect, e.g., with regard to inhibiting the unregulated proliferation of haematological stem cells or slowing down the progression of leukemias, such as chronic myeloid leukemia (CML), acute lymphocyte leukemia (ALL) or acute myeloid leukemia (AML), or the growth of tumors, but also in further surprising beneficial effects, e.g., less side effects, an improved quality of life or a decreased morbidity, compared to a monotherapy applying only one of the pharmaceutically active ingredients used in the combination of the invention.

A further benefit is that lower doses of the active ingredients of the combination of the invention can be used, e.g., that the dosages need not only often be smaller but are also applied less frequently, or can be used in order to diminish the incidence of side effects. This is in accordance with the desires and requirements of the patients to be treated.

Combinations of compounds that inhibit the binding of the Smac protein to IAPs and taxanes may be combined, independently or together, with one or more pharmaceutically acceptable carriers and, optionally, one or more other conventional pharmaceutical adjuvants and administered enterally, e.g., orally, in the form of tablets, capsules, caplets, etc. or parenterally, e.g., intraperitoneally or intravenously, in the form of sterile injectable solutions or suspensions. The enteral and parenteral compositions may be prepared by conventional means.

The combination of compounds that inhibit the binding of the Smac protein to IAPs and taxanes can be used alone or combined with at least one other pharmaceutically active compound for use in these pathologies. These active compounds can be combined in the same pharmaceutical preparation or in the form of combined preparations "kit of parts" in the sense that the combination partners can be dosed independently or by use of different fixed combinations with distinguished amounts of the combination partners, i.e., simultaneously or at different time points. The parts of the kit of parts can then, e.g., be administered simultaneously or chronologically staggered, that is at different time points and with equal or different time intervals for any part of the kit of parts. Non-limiting examples of compounds which can be cited for use in combination with the combination of a compounds that inhibit the binding of the Smac protein to IAPs and taxanes are cytotoxic chemotherapy drugs, such as cytosine arabinoside, daunorubicin, doxorubicin, cyclophosphamide, VP-16, or imatinib etc. Further, the combination of a compounds that inhibit the binding of the Smac protein to IAPs and taxanes could be combined with other inhibitors of signal transduction or other oncogene-targeted drugs with the expectation that significant synergy would result.

The COMBINATION OF THE INVENTION can be a combined preparation or a pharmaceutical composition.

Moreover, the present invention relates to a method of treating a warm-blooded animal having a proliferative disease comprising administering to the animal a COMBINATION OF THE INVENTION in a quantity which is therapeutically effective against said proliferative disease.

Furthermore, the present invention pertains to the use of a COMBINATION OF THE INVENTION for the treatment of a proliferative disease and for the preparation of a medicament for the treatment of a proliferative disease.

Moreover, the present invention provides a commercial package comprising as active ingredients COMBINATION OF THE INVENTION, together with instructions for simultaneous, separate or sequential use thereof in the delay of progression or treatment of a proliferative disease.

Preferred embodiments of the invention are represented by combinations comprising:
  compound I and paclitaxel;
  compound IV and paclitaxel;
  compound I and docetaxel; and
  compound IV and docetaxel.

In further aspects, the present inventions provides:
a combination which comprises:
  (a) a COMBINATION OF THE INVENTION, wherein the active ingredients are present in each case in free form or in the form of a pharmaceutically acceptable salt or any hydrate thereof; and, optionally,
  (b) at least one pharmaceutically acceptable carrier; for simultaneous, separate or sequential use;
a pharmaceutical composition comprising:
  (a) a quantity which is jointly therapeutically effective against a proliferative disease of a COMBINATION OF THE INVENTION; and
  (b) at least one pharmaceutically acceptable carrier;
  the use of a COMBINATION OF THE INVENTION for the treatment of a proliferative disease;
  the use of a COMBINATION OF THE INVENTION for the preparation of a medicament for the treatment of a proliferative disease;
  the use of a COMBINATION OF THE INVENTION wherein the compound that inhibit the binding of the Smac protein to IAPs is a compound of formula (I); and
  the use of COMBINATION OF THE INVENTION wherein the compound that inhibit the binding of the Smac protein to IAPs is a compound of formula (IV).

In particular, the present invention relates to a combination comprising:
  (a) a taxane; and
  (b) a compound that inhibit the binding of the Smac protein to IAPs.

Moreover, in particular, the present invention relates to a combined preparation, which comprises:
  (a) one or more unit dosage forms of a taxane; and
  (b) one or more unit dosage forms of a compound that inhibit the binding of the Smac protein to IAPs.

Furthermore, in particular, the present invention pertains to the use of a combination comprising:
  (a) a taxane; and
  (b) a compound that inhibit the binding of the Smac protein to IAPs for the preparation of a medicament for the treatment of a proliferative disease.

B. Diseases to be Treated

The term "proliferative disease" includes but is not restricted to tumors, psoriasis, restenosis, sclerodermitis and fibrosis.

The term hematological malignancy, refers in particular to leukemias, especially those expressing Bcr-Abl, c-Kit or HDAC (or those depending on Bcr-Abl, c-Kit or HDAC) and includes, but is not limited to, CML and ALL, especially the Philadelphia chromosome positive acute lymphocyte leukemia (Ph+ALL), as well as Imatinib-resistant leukemia. Especially preferred is use of the combinations of the present invention for leukemias, such as CML, ALL or AML. Most especially preferred is use in diseases which show resistance to Imatinib and is sold under the name Gleevec®.

The term "a solid tumor disease" especially means ovarian cancer, breast cancer, cancer of the colon and generally the gastrointestinal tract, cervix cancer, lung cancer, e.g., small-cell lung cancer and non-small-cell lung cancer, head and neck cancer, bladder cancer, cancer of the prostate or Kaposi's sarcoma.

The combinations according to the invention, that inhibit the protein kinase activities mentioned, especially tyrosine protein kinases mentioned above and below, can therefore be used in the treatment of protein kinase dependent diseases. Protein kinase dependent diseases are especially proliferative diseases, preferably benign or especially malignant tumours, e.g., carcinoma of the kidneys, brain, liver, adrenal glands, bladder, breast, stomach (especially gastric tumors), ovaries, colon, rectum, prostate, pancreas, lungs (especially SCLC), vagina or thyroid, sarcoma, multiple myeloma, glioblastomas and numerous tumours of the neck and head, as well as leukemias; especially colon carcinoma or colorectal adenoma, or a tumor of the neck and head, an epidermal hyperproliferation, especially psoriasis, prostate hyperplasia, a neoplasia, especially of epithelial character, preferably mammary carcinoma, or a leukemia. They are able to bring about the regression of tumours and to prevent the formation of tumour metastases and the growth of (also micro) metastases. In addition they can be used in epidermal hyperproliferation, e.g., psoriasis; in prostate hyperplasia; and in the treatment of neoplasias, especially of epithelial character, e.g., mammary carcinoma. It is also possible to use the combinations of the present invention in the treatment of diseases of the immune system insofar as several or, especially, individual tyrosine protein kinases are involved; furthermore, the combinations of the present invention can be used also in the treatment of diseases of the central or peripheral nervous system where signal transmission by at least one tyrosine protein kinase, especially selected from those mentioned specifically, is involved.

In CML, a reciprocally balanced chromosomal translocation in hematopoietic stem cells (HSCs) produces the Bcr-Abl hybrid gene. The latter encodes the oncogenic Bcr-Abl fusion protein. Whereas Abl encodes a tightly regulated protein tyrosine kinase, which plays a fundamental role in regulating cell proliferation, adherence and apoptosis, the Bcr-Abl fusion gene encodes as constitutively activated kinase, which transforms HSCs to produce a phenotype exhibiting deregulated clonal proliferation, reduced capacity to adhere to the bone marrow stroma and a reduces apoptotic response to mutagenic stimuli, which enable it to accumulate progressively more malignant transformations. The resulting granulocytes fail to develop into mature lymphocytes and are released into the circulation, leading to a deficiency in the mature cells and increased susceptibility to infection. ATP-competitive inhibitors of Bcr-Abl have been described which prevent the kinase from activating mitogenic and anti-apoptotic pathways (e.g., P-3 kinase and STAT5), leading to the death of the Bcr-Abl phenotype cells and thereby providing an effective therapy against CML. The combinations of the present invention are thus especially appropriate for the therapy of diseases related to its overexpression, especially leukemias, such as leukemias, e.g., CML or ALL.

In a broader sense of the invention, a proliferative disease includes hyperproliferative conditions, such as leukemias, hyperplasias, fibrosis (especially pulmonary, but also other types of fibrosis, such as renal fibrosis), angiogenesis, psoriasis, atherosclerosis; and smooth muscle proliferation in the blood vessels, such as stenosis or restenosis following angioplasty. In another aspect the combinations of the present invention could be used to treat arthritis.

Combinations of the present invention can also be used to treat or prevent fibrogenic disorders, such as scleroderma (systemic sclerosis); diseases associated with protein aggregation and amyloid formation, such as Huntington's disease; inhibition of the replication of hepatitis C virus and treating hepatitis C virus; treating tumors associated with viral infection, such as human papilloma virus; and inhibiting viruses dependent of heat-shock proteins.

The combinations of the present invention primarily inhibit the growth of blood vessels and are thus, e.g., effective against a number of diseases associated with deregulated angiogenesis, especially diseases caused by ocular neovascularisation, especially retinopathies, such as diabetic retinopathy or age-related macula degeneration; psoriasis; haemangioblastoma, such as haemangioma; mesangial cell proliferative disorders, such as chronic or acute renal diseases, e.g., diabetic nephropathy; malignant nephrosclerosis; thrombotic microangiopathy syndromes or transplant rejection; or especially inflammatory renal disease, such as glomerulonephritis, especially mesangioproliferative glomerulonephritis; haemolytic-uraemic syndrome; diabetic nephropathy; hypertensive nephrosclerosis; atheroma; arterial restenosis; autoimmune diseases; diabetes; endometriosis; chronic asthma; and especially neoplastic diseases (solid tumors, but also leukemias and other haematological malignancies), such as especially breast cancer, cancer of the colon, lung cancer (especially small-cell lung cancer), cancer of the prostate or Kaposi's sarcoma. Combinations of the present invention inhibit the growth of tumors and are especially suited to preventing the metastatic spread of tumors and the growth of micrometastases.

Combinations of the present invention may in particular be used to treat:
(i) a breast tumor; an epidermoid tumor, such as an epidermoid head and/or neck tumor or a mouth tumor; a lung tumor, e.g., a small cell or non-small cell lung tumor; a gastrointestinal tumor, e.g., a colorectal tumor; or a genitourinary tumor, e.g., a prostate tumor, especially a hormone-refractory prostate tumor;
(ii) a proliferative disease that is refractory to the treatment with other chemotherapeutics; or
(iii) a tumor that is refractory to treatment with other chemotherapeutics due to multi-drug resistance.

Example 1

The combination of Docetaxel with a compound of formula (III) in the ovarian carcinoma line SKOV3 results in significant synergy in vitro. FIG. 1 indicates anti-proliferative activity of compound of formula (III) alone (bottom row), Docetaxel alone (most leftward column) and combinations of the two agents across a dose range.

Figure 2:
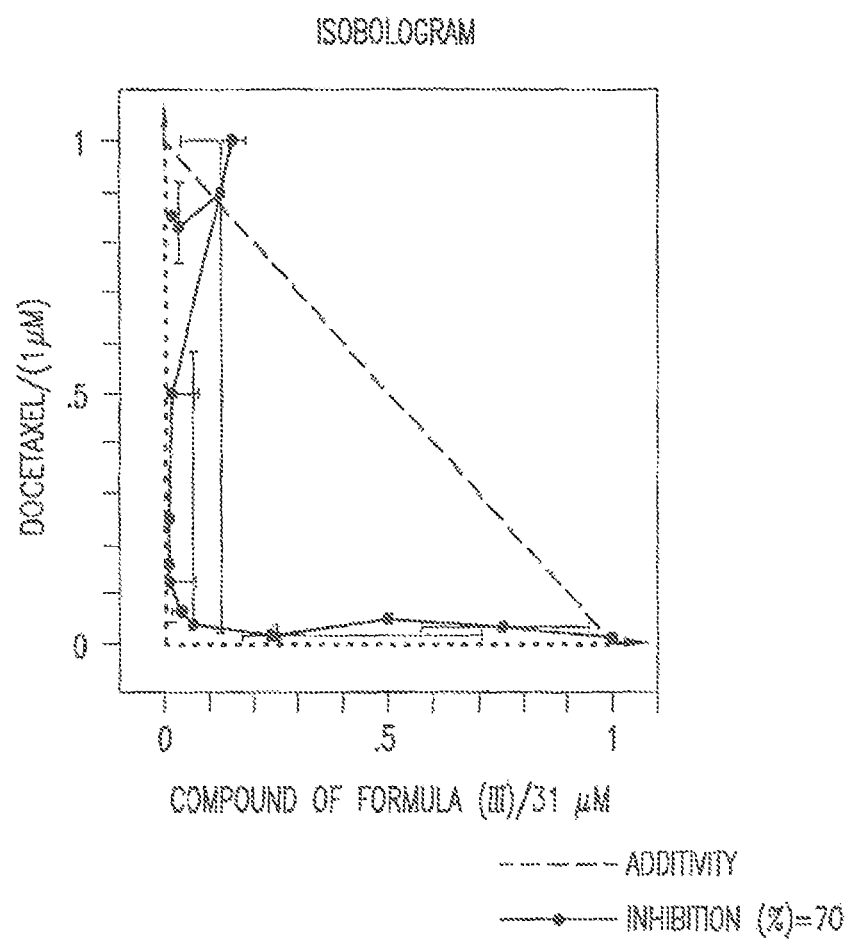
FIG. 2 is the isobologram at 70% growth inhibition for Example 1.

FIG. 2 is the corresponding isobologram at 70% growth inhibition.

Example 2

Figure 3:
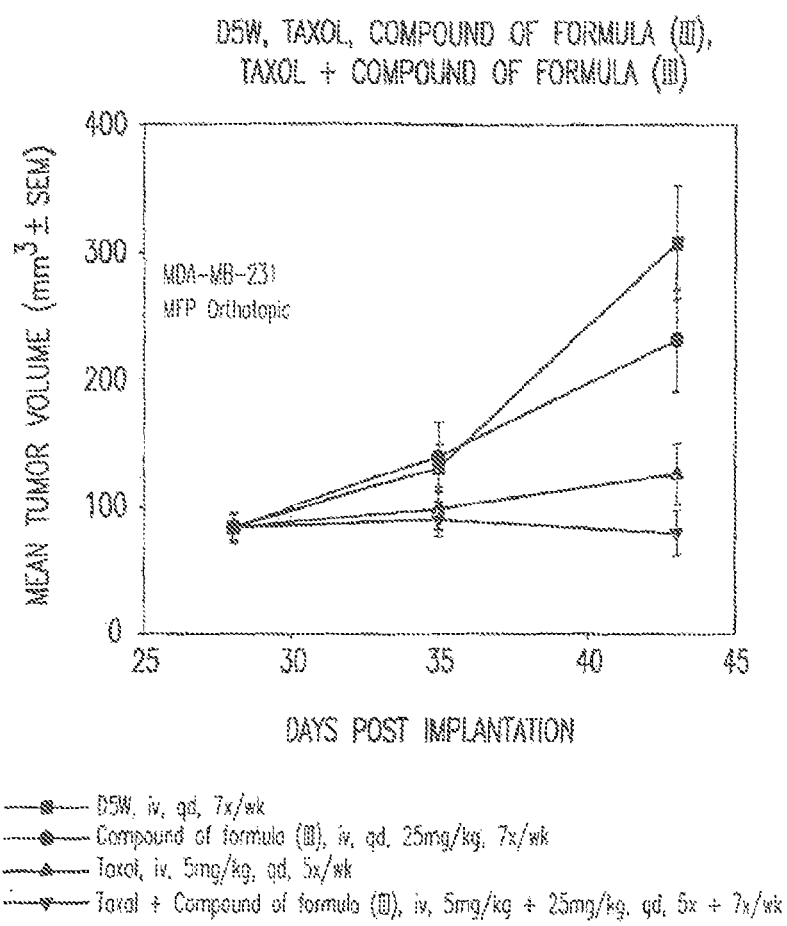
FIG. 3 illustrate that the combination of a compound of formula (III) and Paclitaxel has superior anti-tumor activity compared to either agent administered as a single agent in the orthotopic breast cancer model MDA-MB-231. Established tumors were treated for two weeks with the dose regimens are indicated.

The combination of a compound of formula (III) and Paclitaxel has superior anti-tumor activity compared to either agent administered as a single agent in the orthotopic breast cancer model MDA-MB-231. Established tumors were treated for two weeks with the dose regimens indicated in FIG. 3.

Example 3

Figure 4:
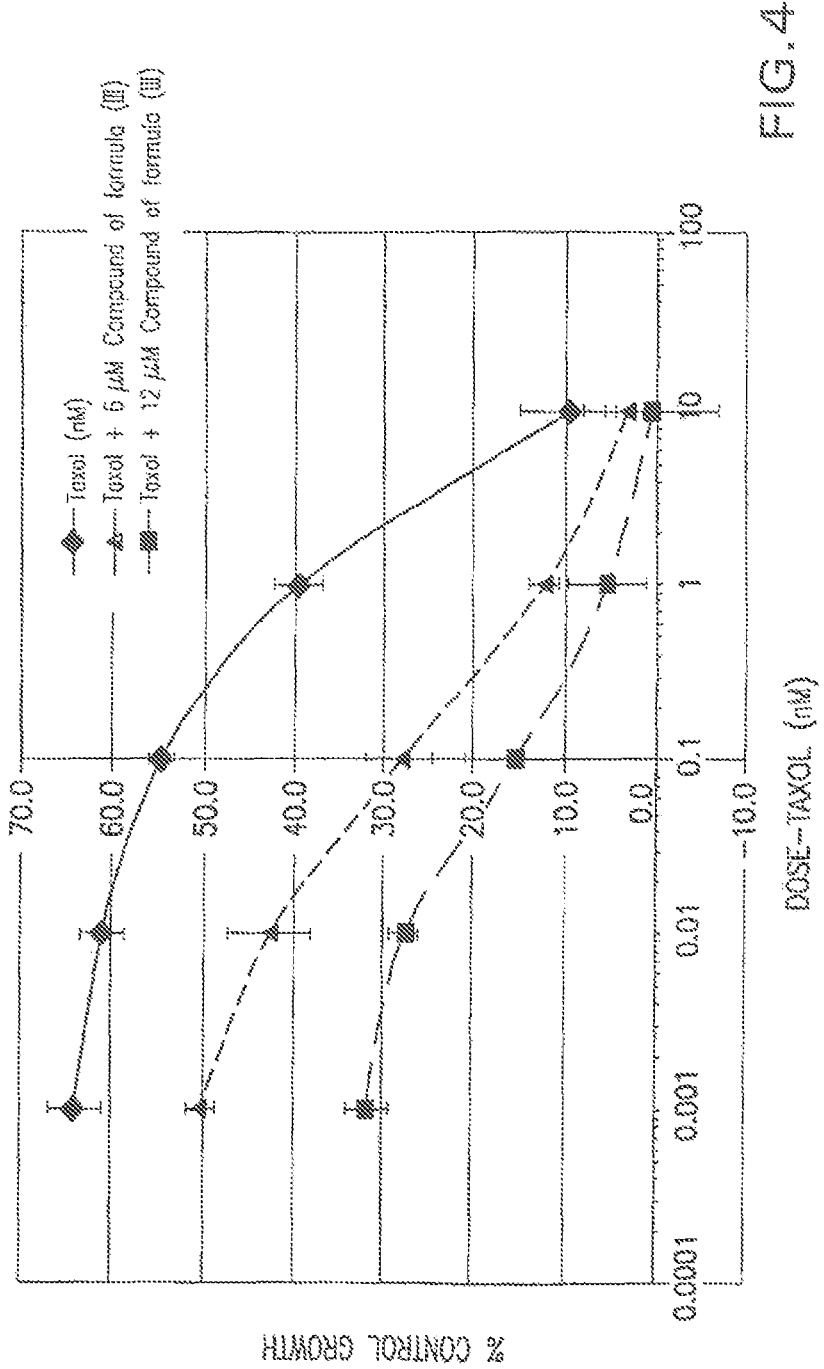
FIG. 4 illustrates that the anti-proliferative activity of Taxol is dramatically enhanced by combination with a compound of formula (III) in the melanoma cell line A375. Top curve shows dose response of Taxol alone in A375 in three day proliferation assay. Bottom two curves show Taxol dose response in presence of either 6 μM or 12 μM compound of formula (III).

FIG. 4 indicates anti-proliferative activity of Taxol is dramatically enhanced by combination with a compound of formula (III) in the melanoma cell line A375. Top curve shows dose response of Taxol alone in A375 in three day proliferation assay. Bottom two curves show Taxol dose response in presence of either 6 µM or 12 µM compound of formula (III).

The compound of formula (III) has no stand alone activity in A375 (data not shown).

Example 4

IAP Inhibitor compounds such as LBW242 display single agent activity on a limited number of tumor cell lines in vitro. To determine whether a larger number of cell lines are responsive to an IAP Inhibitor in combination with Taxol, Taxol dose response evaluations are performed in the presence or absence of LBW242 with 10-12 tumor cell lines representing the following cancers: lung, ovarian, melanoma, pancreatic. The criteria used for an assignment of combination activity—either additivity or synergy—is a minimum of a five fold potency shift for the IC50 of Taxol in combination with LBW242 relative to Taxol alone. Tumor cell lines which are responsive to LBW242 as a monotherapy such as MDA231 and SKOV3 also exhibit combination activity with Taxol. In all cancer types tested, tumor cell lines are identified in which the IAP Inhibitor compound has no single agent activity yet enhances the response to Taxol. Thus, the range of tumor cell lines sensitive to LBW242 in combination with a cytotoxic agent is slightly larger than the range responsive as a single agent.

LBW242, LCJ917, LCP656 and LCL161 are Smac mimetic small molecules with nM affinity for the BIR3 domain of XIAP and CIAP1. As Inhibitor of Apoptosis Proteins (IAPs) are thought to protect tumor cells from apoptotic cell death, it was anticipated that such agents would sensitize tumor cells to apoptotic stimuli. Interestingly, such agents have anti-proliferative/apoptosis inducing activity as single agents against a narrow range of tumor cell lines for reasons which remain unclear. To determine whether the spectrum of tumor cell lines which responded to these agents would be wider in combination with the cytotoxic drug Taxol, we subject panels of tumor cell lines representing a number of human cancers to in vitro combination analyses.

Materials and Methods

MTS Reagent (#G1111; Promega) in PBS, pH 6-6.5. Phenazine Methosulfate (PMS) (#P-5812; Sigma). 96 well tissue culture plates (#3585; Corning Costar). RPMI 1640 cell culture medium (#22400-071; Invitrogen). Penicillin/Streptomycin (#15140-122; Invitrogen). Fetal Bovine Serum (#10082-139; Invitrogen). (Note: RPMI 1640+10% FBS+Penicillin/Streptomycin is "RPMI/10% FBS Complete medium"). 0.25% Trypsin-EDTA (#25200-056; Invitrogen). The IAP Inhibitor compounds LBW242, LCJ917, LCP656 and LCL161 are dissolved in DMSO at a concentration of 10 mM and stored at −20° C. Tumor Cell Lines are purchased from ATCC.

MTS Assay

Cell proliferation/cell death is analyzed in 72 hr. 3-(4,5-dimethylthiazol-2-yl)-5-(3-carboxymethoxyphenyl)-2-(4-sulfophenyl)-2H-tetrazolium, inner salt (MTS) assays. Tumor cell lines are plated at subconfluent densities in 96 well plate format and allowed to adhere for 12-16 hr. Cpds are then added according to the following schemes: i.

Chemotherapeutic agents or cytotoxic cpds (Ctx) are added alone, in an 8-point/10-fold titration scheme from high to low dose, in triplicate. ii. IAP-inhibitor (NVP-LBW242) is added alone, at a single fixed dose (dose determined in stand alone MTS assays) in triplicate. iii. Ctx agent (8-point/10-fold scheme) and LBW242 (single fixed dose) are added together, simultaneously, in triplicate. Once all dosing is completed, cells are cultured for a further 72 hr. and then assayed using the MTS format:

Day −1

1. Plate cells in RPMI/10% FBS Complete medium. Set-up Time 0 (T.0) and

Experimental (EXP) plates as appropriate for each cell line. Each plate will contain culture medium (CM) alone (Blank) wells (200 ul/well).

2. An additional "Blank" plate will contain Blank wells: the center 24 wells will contain 12 wells with 100 ul CM/well and 12 wells with 110 ul CM/well. All surrounding wells will contain 200 ul CM/well.

3. Trypsinize cells at 37° c./5% CO2 for up to 5', quench the trypsin with CM and then plate cells onto 96 well plates at 90 ul/well. Seed cells at densities appropriate for each cell line (appropriate cell densities will yield optimal cell growth which is reflected in T.0 OD 490 values between 0.3-0.8). Add 90 ul CM to 6 Blank wells on the T.0 plate and 200 ul CM to all surrounding wells. Add 200 ul CM to all outer wells on Exp plates. Culture plates @ 37° C./5% CO2 for 24 (T.0 plate) to 96 hr. (EXP plates).

Day 0

1. Add MTS/PMS reagents to T.0 Plate(s). Mix enough of each reagent (100 ul 500 uM PMS per 2 ml 333 ug/ml MTS reagent/96 well plate) for 20 ul/well. Add 20 ul mixture to ea. well & incubate plate(s) 2 hr. @ 37° C./5% CO2. Read OD 490 nm using SoftMax Pro software on a Molecular Devices (Sunnyvale, Calif.) Spectrophotometer. Calculate T.0 values for each cell line to be assayed by generating the mean value of the OD 490 nm readings from each cell line's T.0 wells (6/cell line) and subtracting the mean OD 490 nm values from Blank wells.

2. Dose EXP plate(s) with appropriate Cdps in triplicate in the schemes shown in FIG. 5. Incubate plates at 37° C./5% CO2 for 72 hr.

Day 3

1. Add MTS/PMS reagents to EXP Plate(s). Mix enough of each reagent (100 ul 500 uM PMS per 2 ml 333 ug/ml MTS reagent/96 well plate) for 20 ul/well. Add 20 ul mixture to ea. well & incubate plate(s) 2 hr. @ 37° C./5% CO2. Read OD 490 nm using SoftMax Pro software on a Molecular Devices Spectrophotometer. MTS Data is generated as described below:

Calculate % CG by first averaging triplicate results (subtracting blank medium values) as follows:

If $OD$ treated$>OD$ $T.0$, then: % $CG = 100 \times [(OD$ treated$-OD$ $T.0)/(OD$ 72 hr. untreated$-OD$ $T.0)]$ If $OD$ treated$<OD$ $T.0$, then: % $CG = 100 \times [(OD$ treated$-OD$ $T.0)/OD$ $T.0]$ Selection of IAP Inhibitor Dose Levels IAP Inhibitors are used at a single fixed dose of 10 uM (12 uM in earliest assays) in lines where compound shows no effect (IC50>10 uM) as a single agent.

IAP Inhibitors are used at a single fixed dose yielding 70-80% control cell growth (% CG) (between IC20-IC30 dose) in lines where compounds show moderate stand alone activity (IC50 1-10 uM) as a single agent.

In most cases, fixed doses in specific cell lines are set by generating empirical data in MTS assays.

Criteria for Call of Combination Activity

Combinations exhibiting a 5-fold potency shift in the IC50 dose as compared with Taxol alone are scored as a combination activity hits provided that under similar conditions LBW242 by itself did not result in <70% CG (IC30).

True assessment of synergy requires fixed ratio titrations of combination partners and determination of combination indices. The above criteria do not formally distinguish between synergy and additivity.

Figure 5:
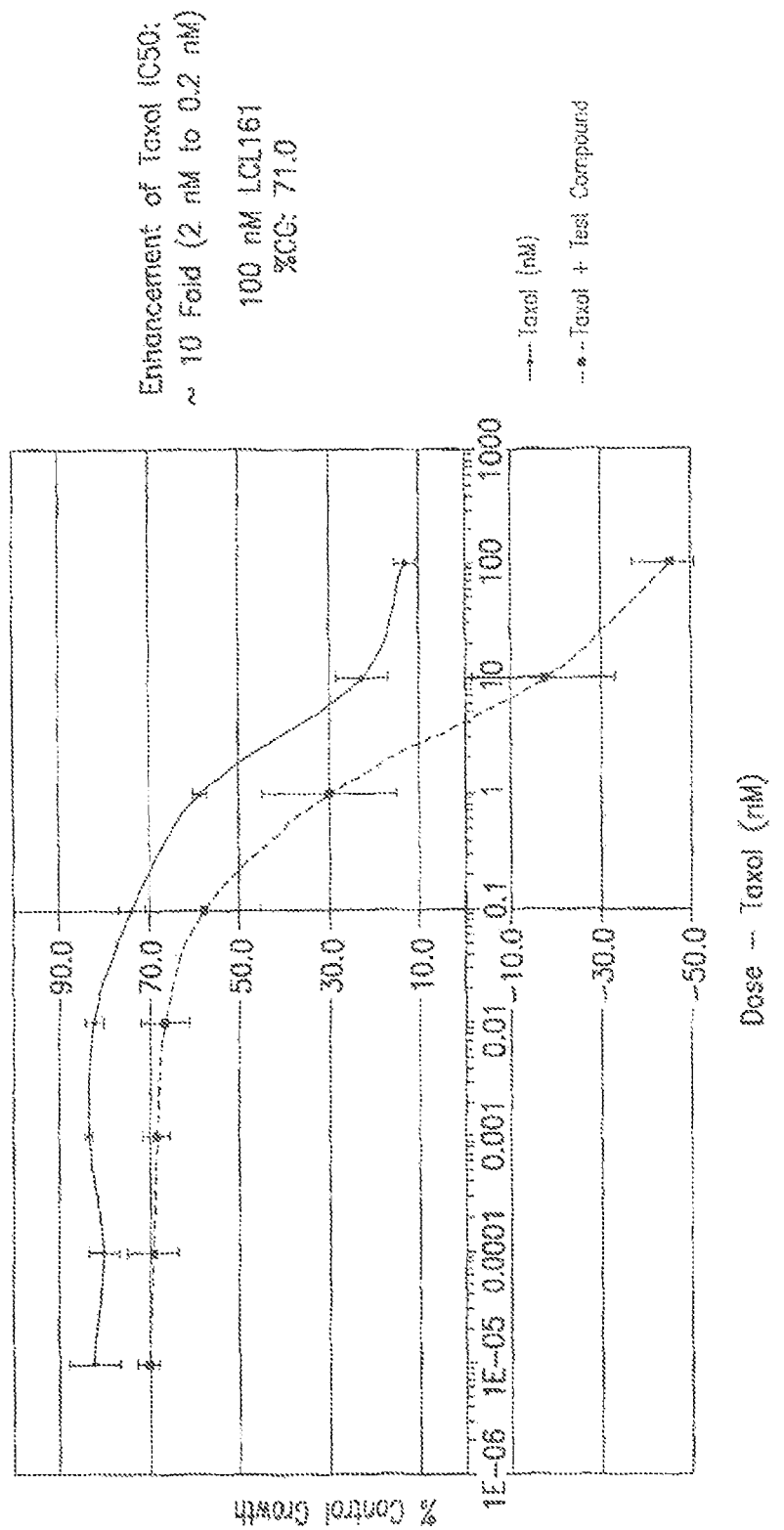
FIG. 5 illustrates Taxol+100 nM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in OVCAR-4.

Ovarian Tumor Cell Lines:

FIG. 5 Taxol+100 nM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in OVCAR-4

Figure 6:
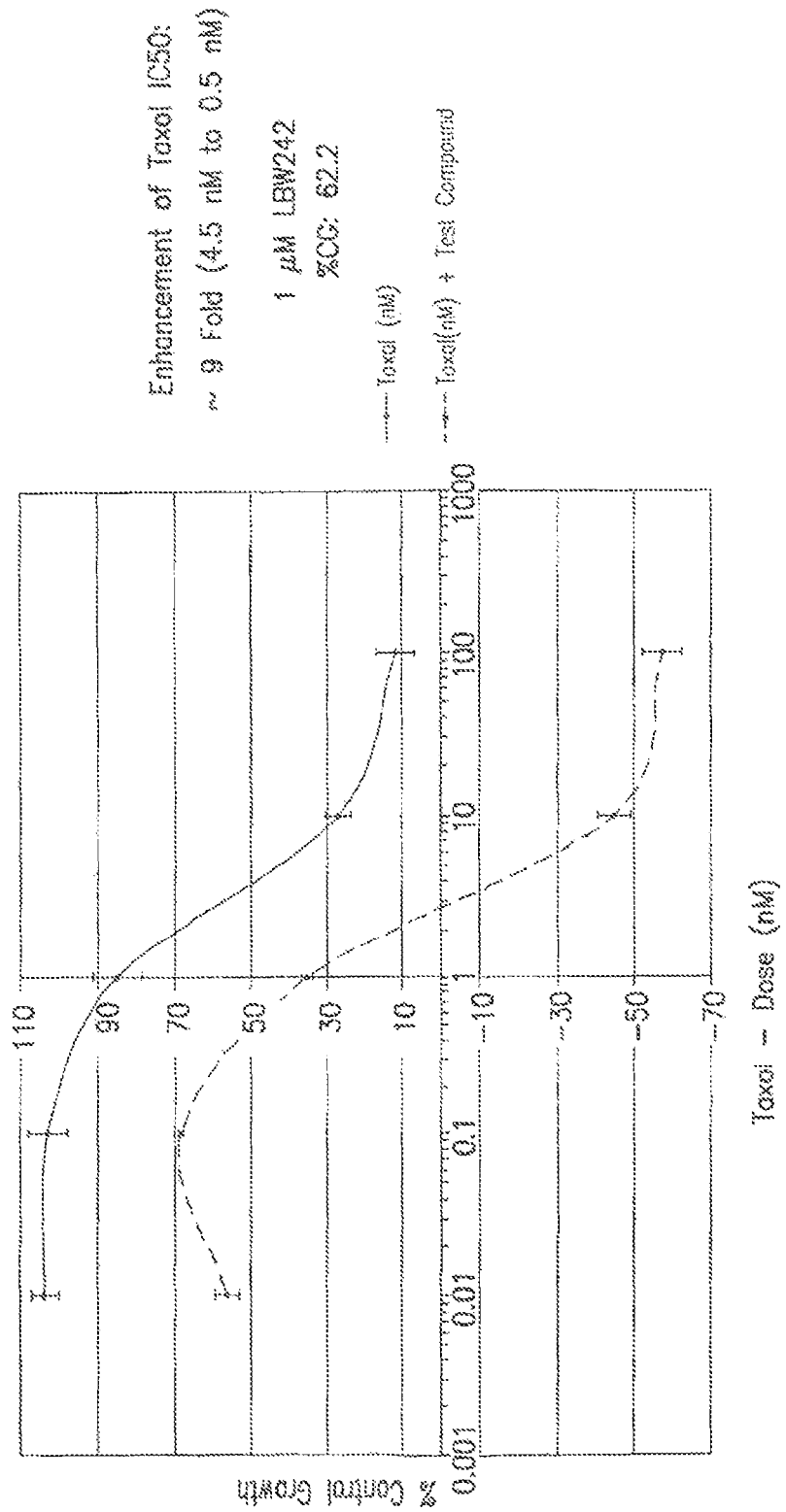
FIG. 6 illustrates Taxol+1 uM N-[1-Cyclohexyl-2-oxo-2-(6-phenethyl-octahydro-pyrrolo[2,3-c]pyridin-1-yl)-ethyl]-2-methylamino-propionamide Combination in OVCAR-4.

FIG. 6 Taxol+1 uM N-[1-Cyclohexyl-2-oxo-2-(6-phenethyl-octahydro-pyrrolo[2,3-c]pyridin-1-yl)-ethyl]-2-methylamino-propionamide Combination in OVCAR-4

Figure 7:
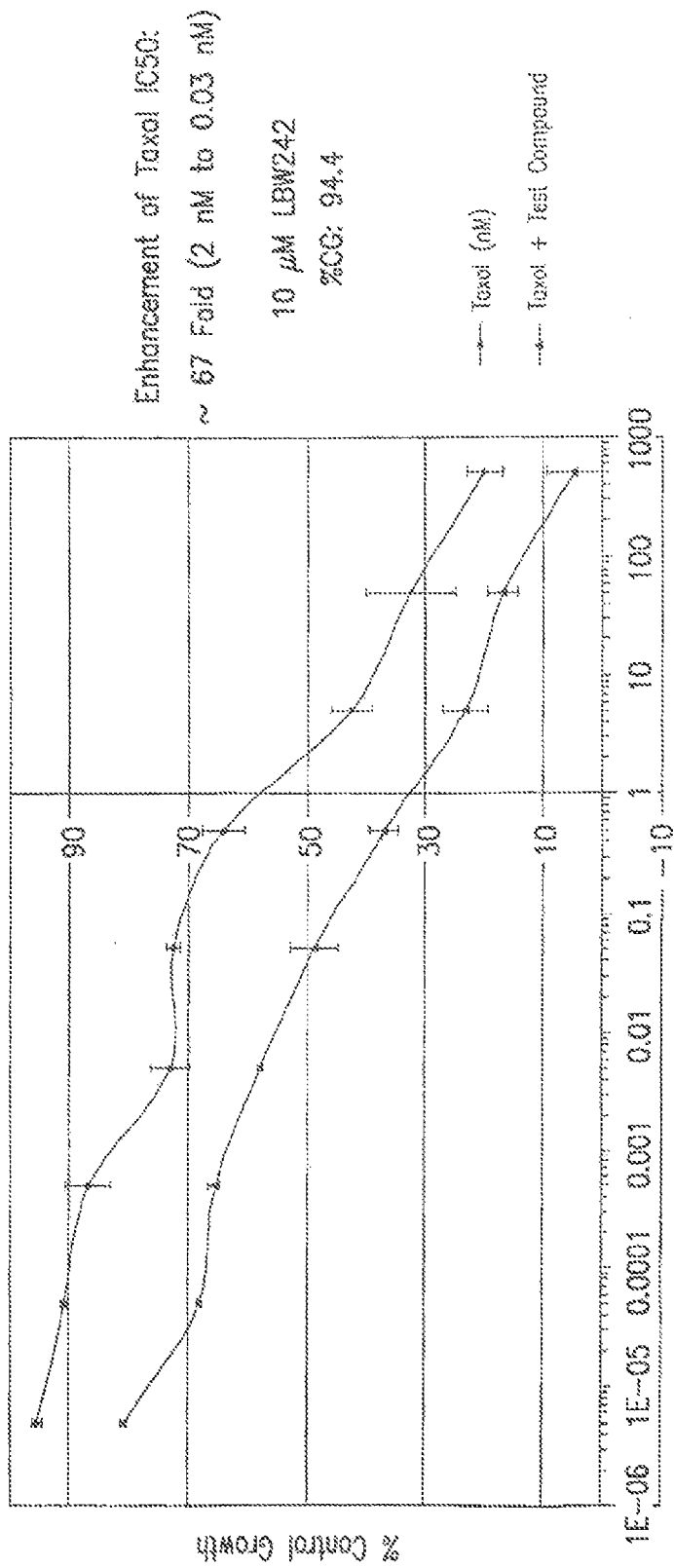
FIG. 7 illustrates Taxol+10 uM N-[1-Cyclohexyl-2-oxo-2-(6-phenethyl-octahydro-pyrrolo[2,3-c]pyridin-1-yl)-ethyl]-2-methylamino-propionamide Combinations in TOV 21G.
Figure 8:
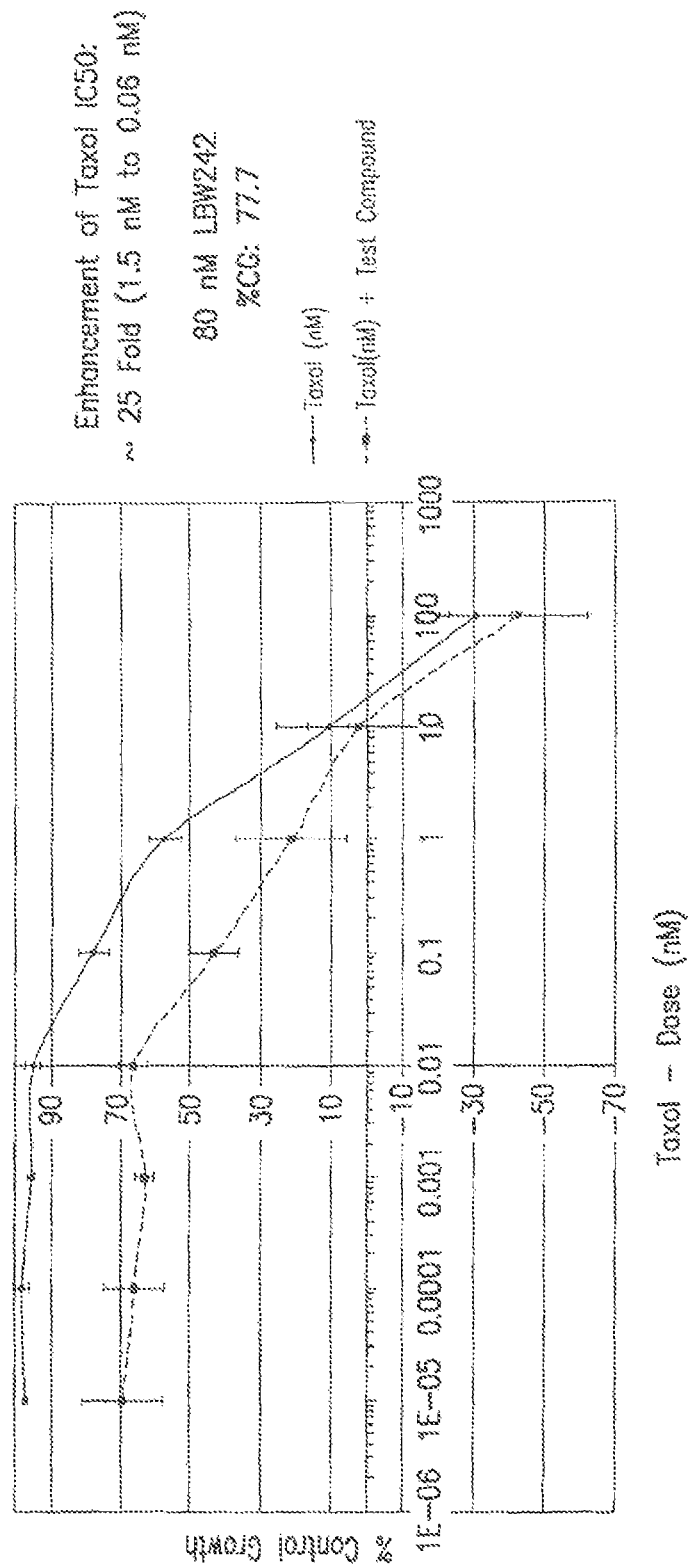
FIG. 8 illustrates Taxol+80 nM N-[1-Cyclohexyl-2-oxo-2-(6-phenethyl-octahydro-pyrrolo[2,3-c]pyridin-1-yl)-ethyl]-2-methylamino-propionamide Combinations in SKOV-3.

FIG. 7 Taxol+10 uM N-[1-Cyclohexyl-2-oxo-2-(6-phenethyl-octahydro-pyrrolo[2,3-c]pyridin-1-yl)-ethyl]-2-methylamino-propionamide Combinations in TOV 21G FIG. 8 Taxol+80 nM N-[1-Cyclohexyl-2-oxo-2-(6-phenethyl-octahydro-pyrrolo[2,3-c]pyridin-1-yl)-ethyl]-2-methylamino-propionamide Combinations in SKOV-3

Figure 9:
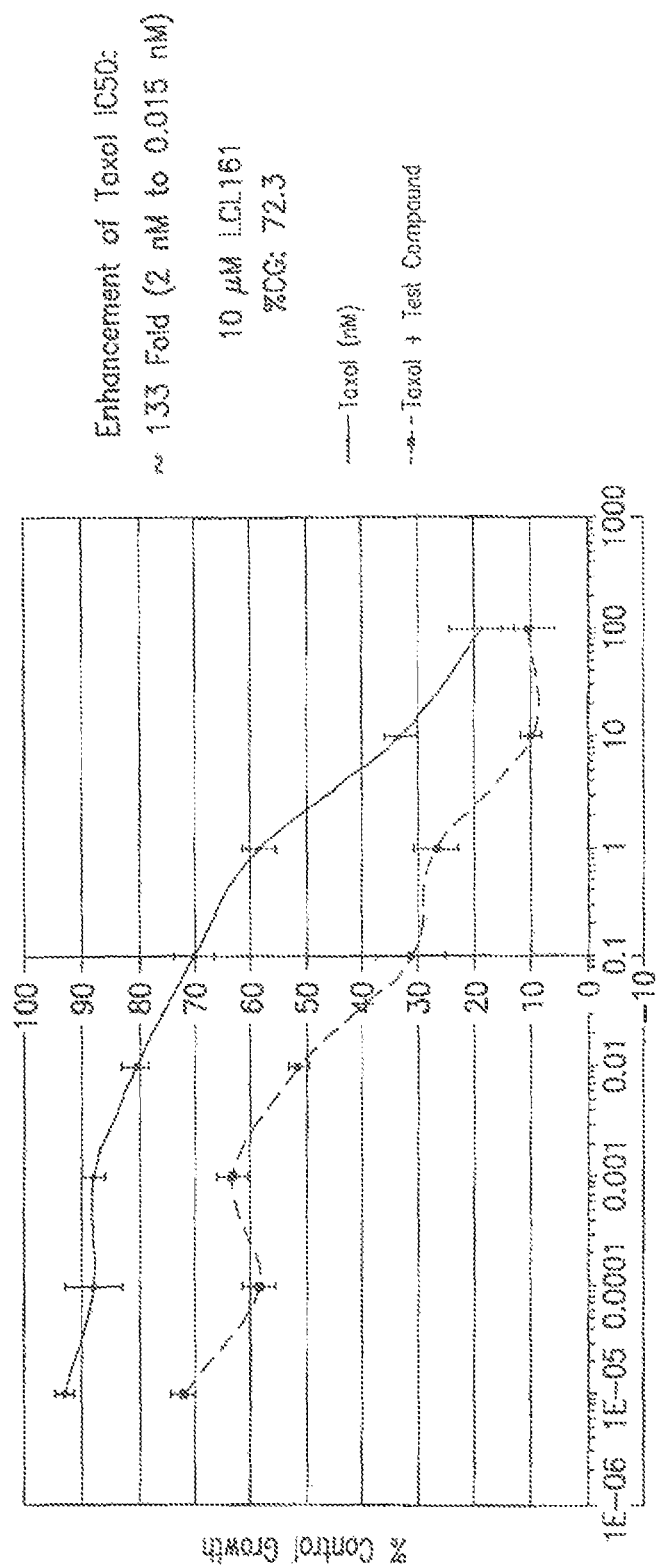
FIG. 9 illustrates Taxol+10 uM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in SKMEL-2.

Melanoma Cancer Cell Lines:

FIG. 9 Taxol+10 uM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in SKMEL-2

Figure 10:
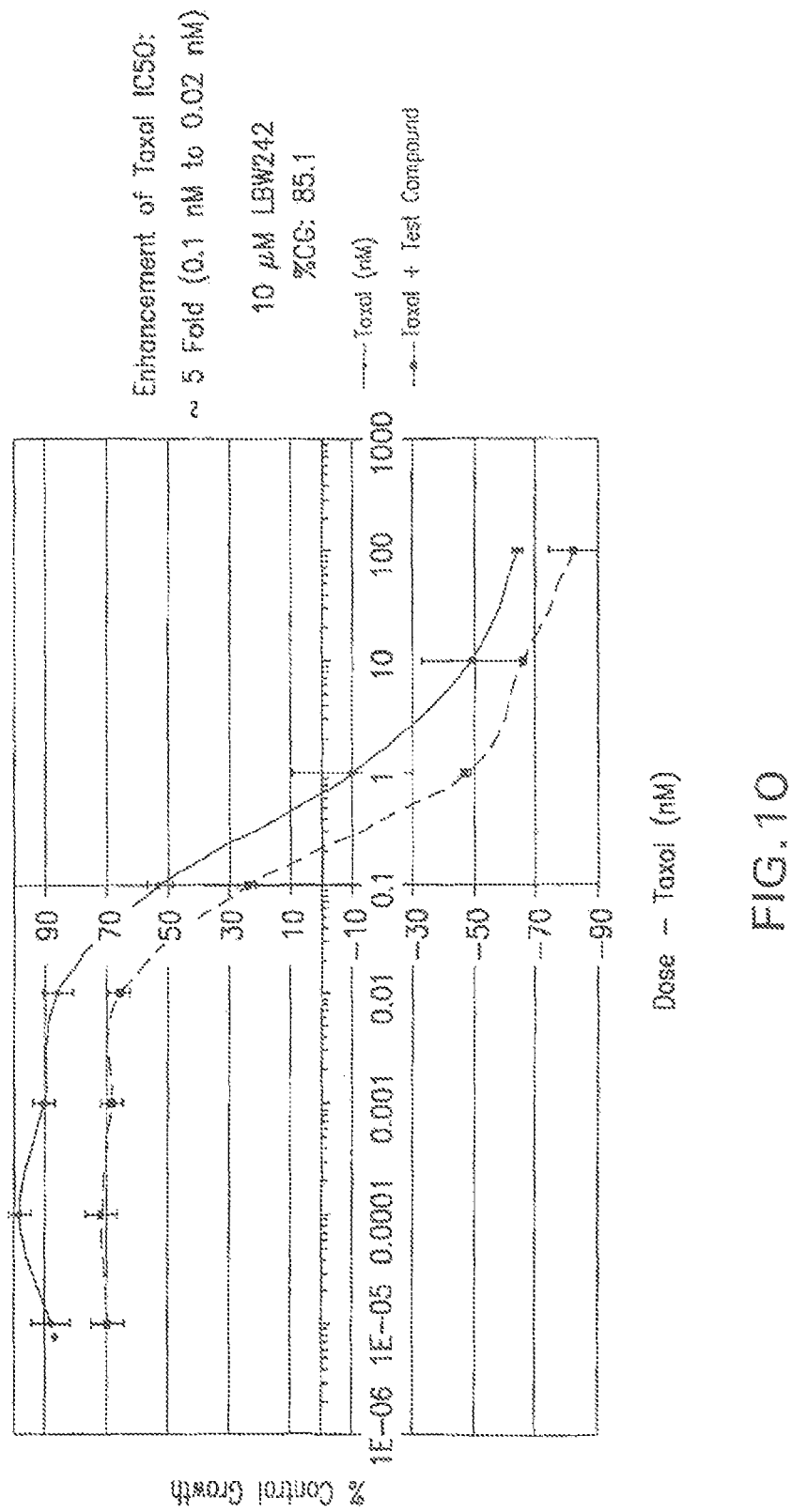
FIG. 10 illustrates Taxol+10 uM N-[1-Cyclohexyl-2-oxo-2-(6-phenethyl-octahydro-pyrrolo[2,3-c]pyridin-1-yl)-ethyl]-2-methylamino-propionamide Combination in SKMEL-2.

FIG. 10 Taxol+10 uM N-[1-Cyclohexyl-2-oxo-2-(6-phenethyl-octahydro-pyrrolo[2,3-c]pyridin-1-yl)-ethyl]-2-methylamino-propionamide Combination in SKMEL-2

Figure 11:
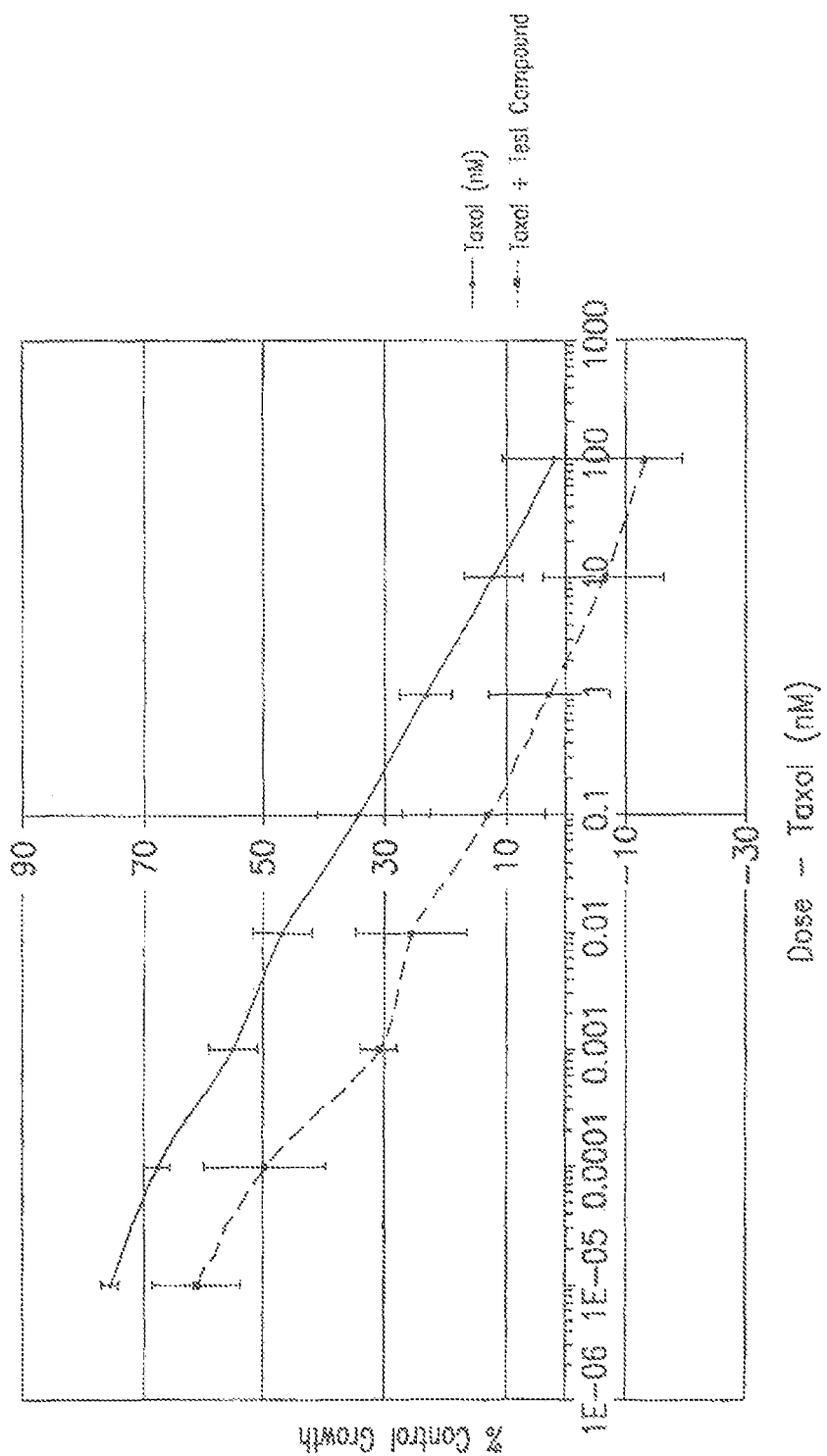
FIG. 11 illustrates Taxol+10 uM N-[1-Cyclohexyl-2-oxo-2-(6-phenethyl-octahydro-pyrrolo[2,3-c]pyridin-1-yl)-ethyl]-2-methylamino-propionamide Combination in MEWO.
Figure 12:
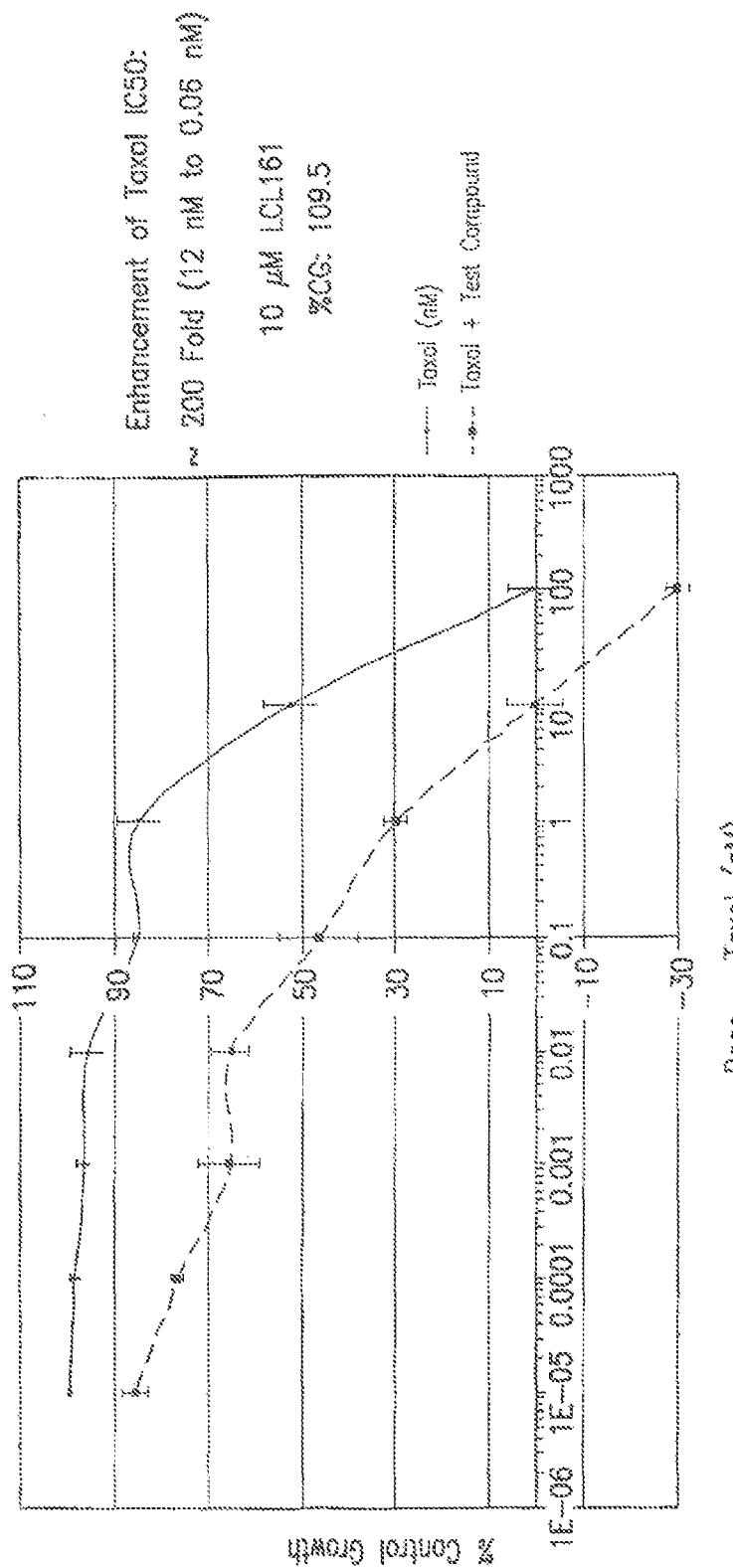
FIG. 12 illustrates Taxol+10 uM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in A375.

FIG. 11 Taxol+10 uM N-[1-Cyclohexyl-2-oxo-2-(6-phenethyl-octahydro-pyrrolo[2,3-c]pyridin-1-yl)-ethyl]-2-methylamino-propionamide Combination in MEWO FIG. 12 Taxol+10 uM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in A375

Figure 13:
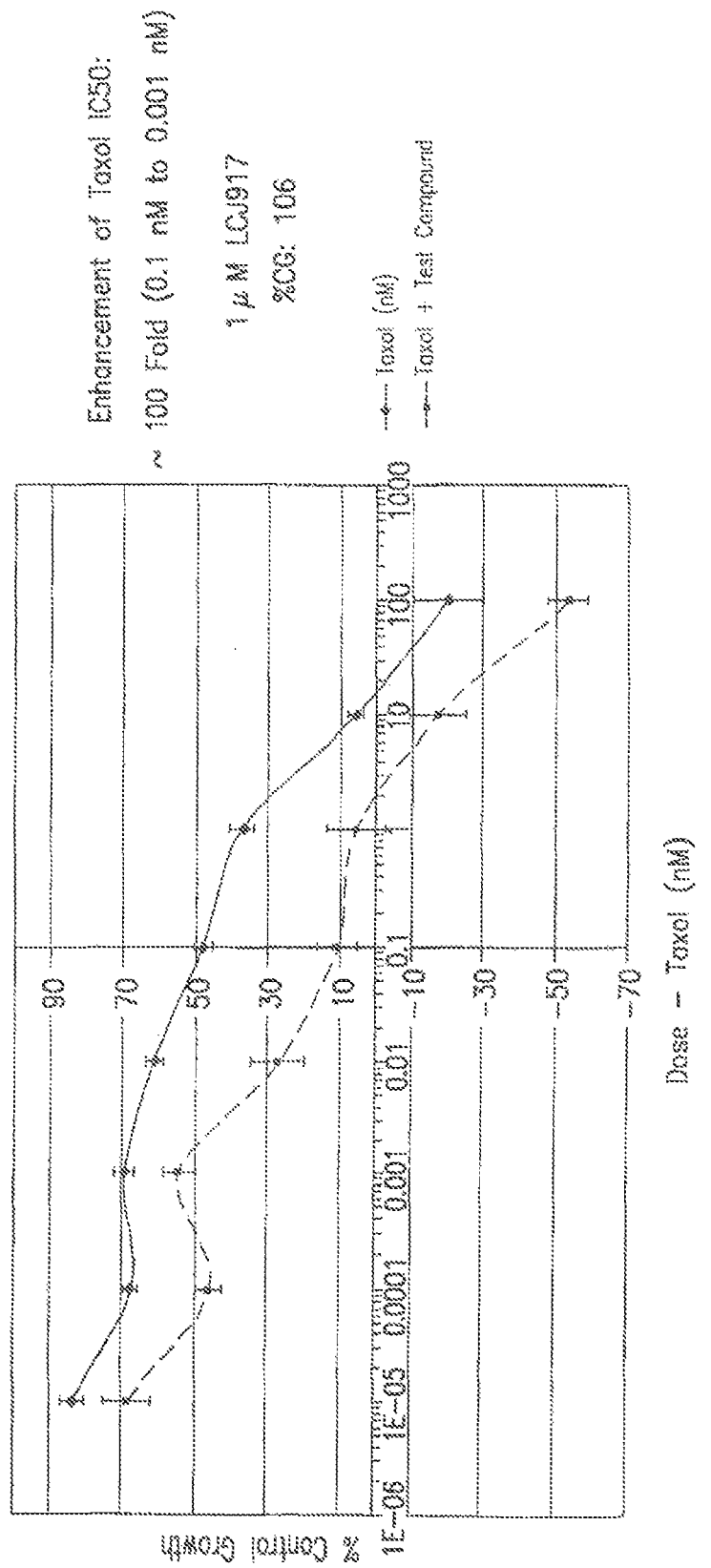
FIG. 13 illustrates Taxol+1 uM N-[1-Cyclohexyl-2-(2-{2-[(4-fluoro-phenyl)-methyl-amino]-pyridin-4-yl}-pyrrolidin-1-yl)-2-oxo-ethyl]-2-methylamino-propionamide Combination in A375.

FIG. 13 Taxol+1 uM N-[1-Cyclohexyl-2-(2-{2-[(4-fluoro-phenyl)-methyl-amino]-pyridin-4-yl}-pyrrolidin-1-yl)-2-oxo-ethyl]-2-methylamino-propionamide Combination in A375

Figure 14:
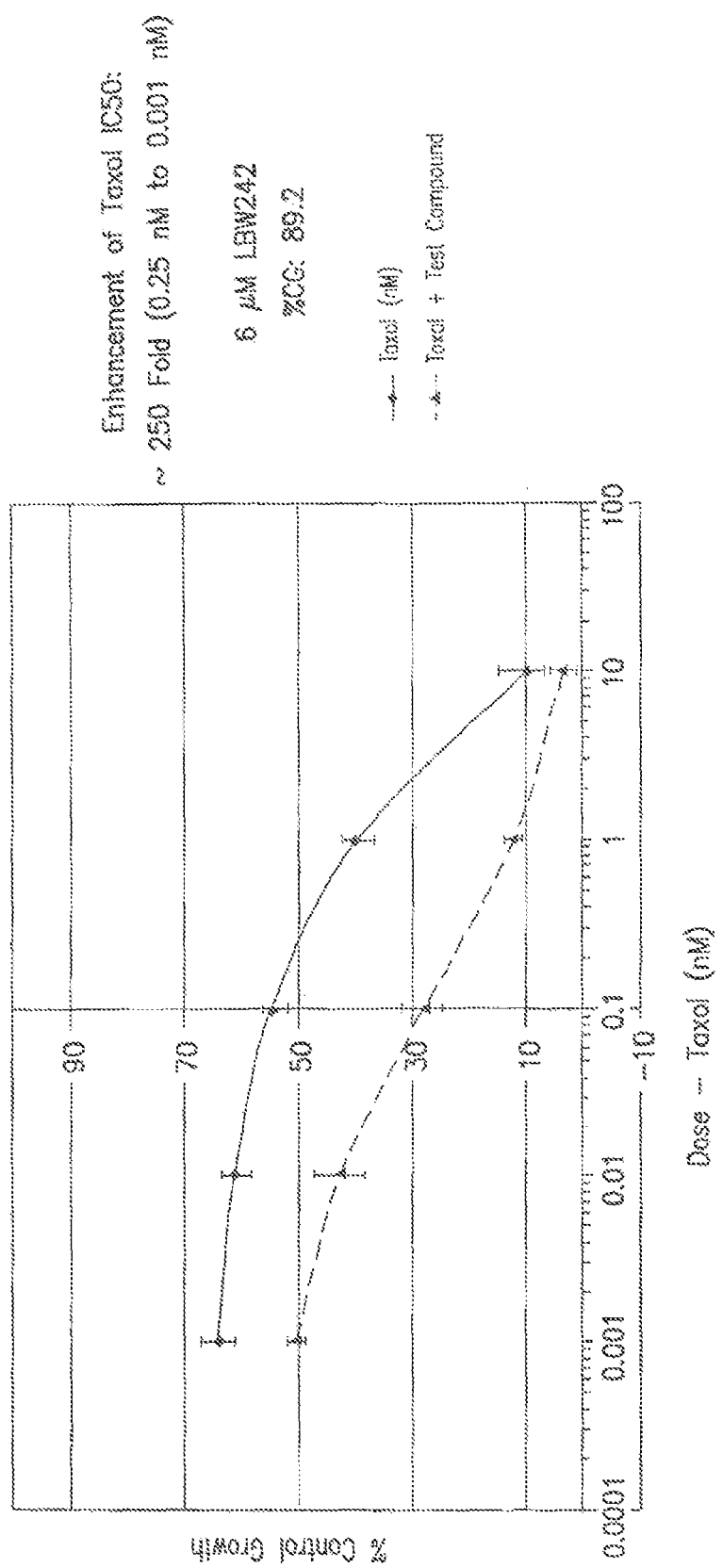
FIG. 14 illustrates Taxol+6 uM N-[1-Cyclohexyl-2-oxo-2-(6-phenethyl-octahydro-pyrrolo[2,3-c]pyridin-1-yl)-ethyl]-2-methylamino-propionamide Combination in A375.

FIG. 14 Taxol+6 uM N-[1-Cyclohexyl-2-oxo-2-(6-phenethyl-octahydro-pyrrolo[2,3-c]pyridin-1-yl)-ethyl]-2-methylamino-propionamide Combination in A375

Figure 15:
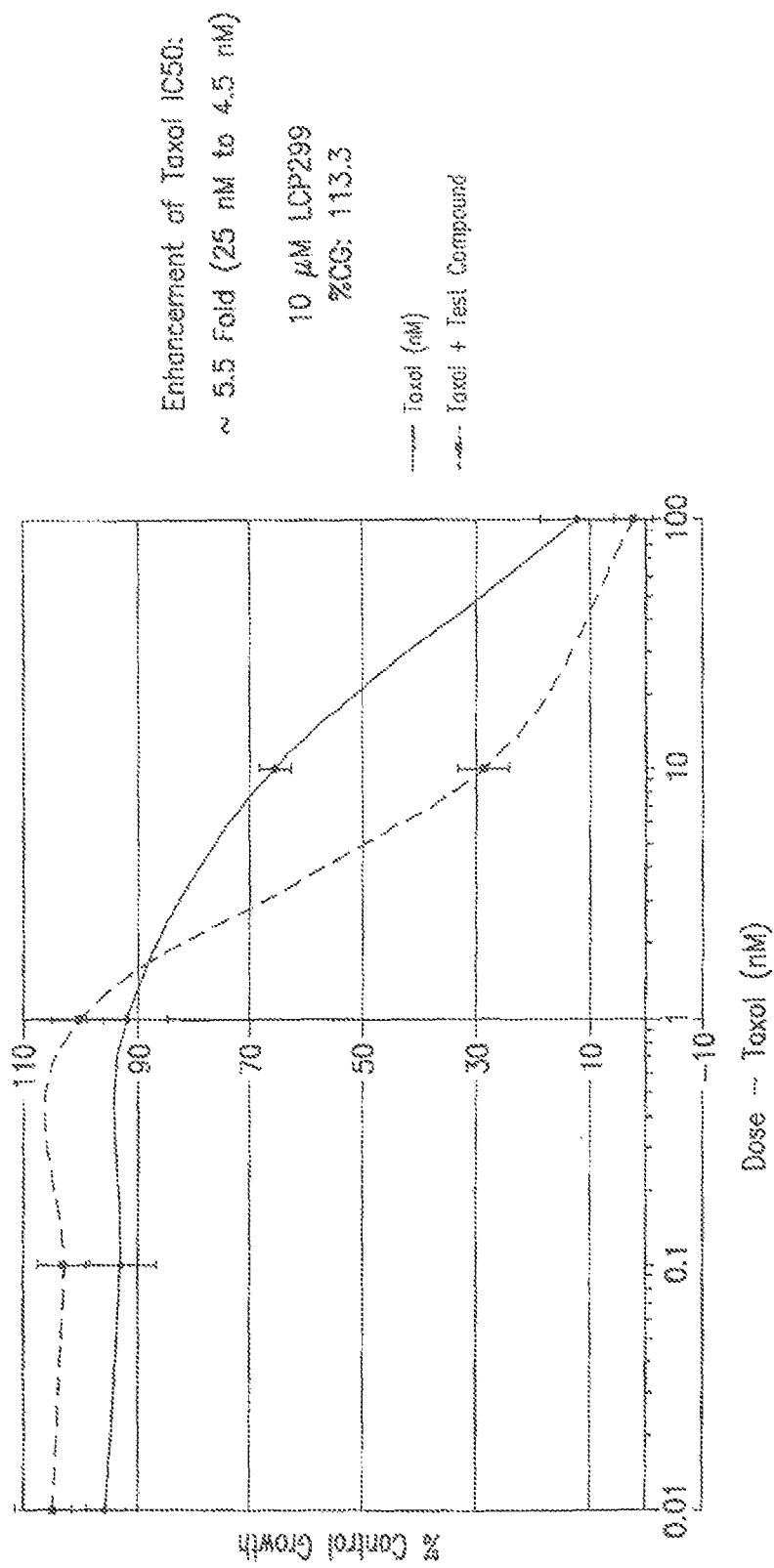
FIG. 15 illustrates Taxol+10 uM N-(1-Cyclohexyl-2-{2-[5-(4-fluoro-benzoyl)-pyridin-3-yl]-pyrrolidin-1-yl}-2-oxo-ethyl)-2-methylamino-propionamide Combination in A375.

FIG. 15 Taxol+10 uM N-(1-Cyclohexyl-2-{2-[5-(4-fluoro-benzoyl)-pyridin-3-yl]-pyrrolidin-1-yl]-2-oxo-ethyl)-2-methylamino-propionamide Combination in A375

Figure 16:
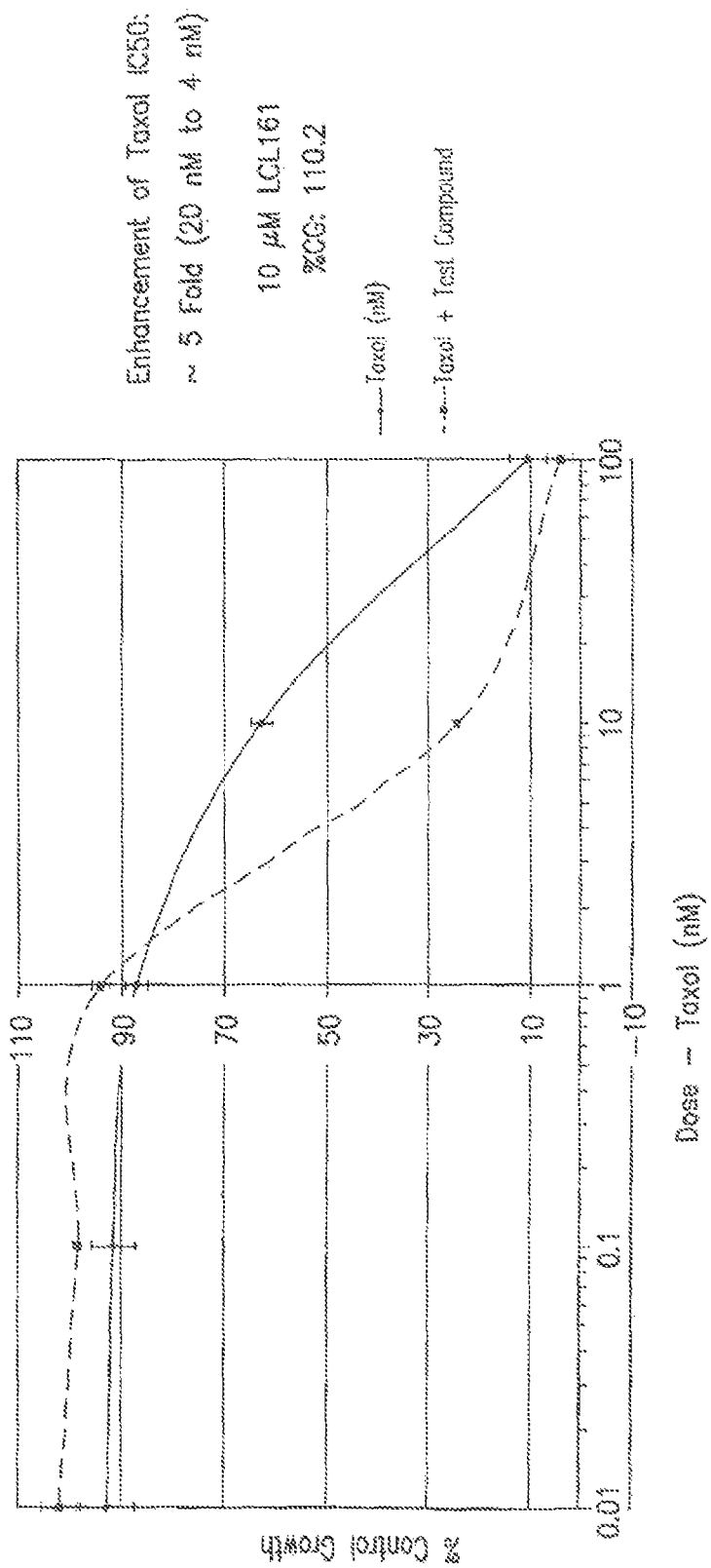
FIG. 16 illustrates Taxol+10 uM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in A375.

FIG. 16 Taxol+10 uM N-(1-Cyclohexyl-2-{2-[4-(4-fluoro-benzoyl)-thiazol-2-yl}-pyrrolidin-1-yl]-2-oxo-ethyl)-2-methylamino-propionamide Combination in A375

Figure 17:
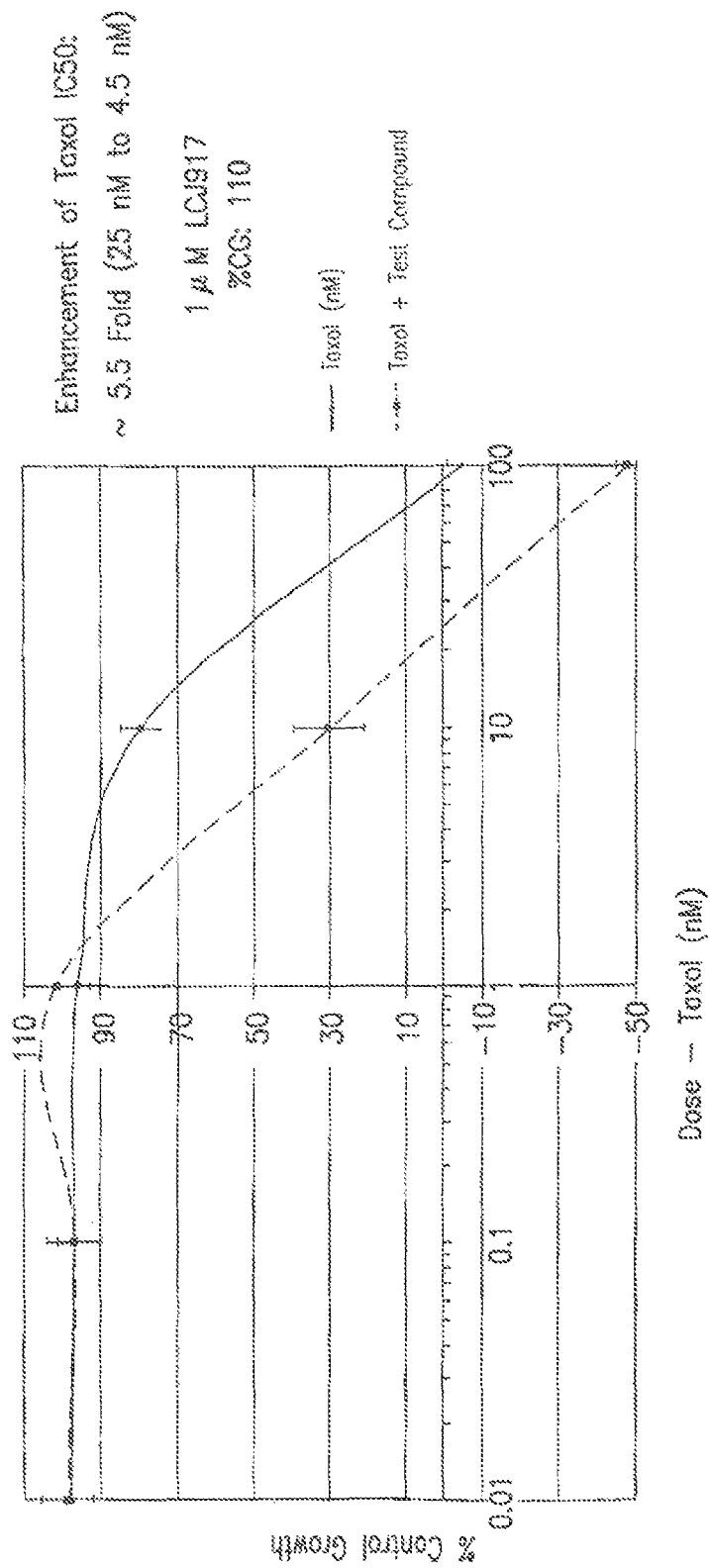
FIG. 17 illustrates Taxol+1 uM N-[1-Cyclohexyl-2-(2-{2-[(4-fluoro-phenyl)-methyl-amino]-pyridin-4-yl}-pyrrolidin-1-yl)-2-oxo-ethyl]-2-methylamino-propionamide Combination in A375.

FIG. 17 Taxol+1 uM N-[1-Cyclohexyl-2-(2-{2-[(4-fluoro-phenyl)-methyl-amino]-pyridin-4-yl}-pyrrolidin-1-yl)-2-oxo-ethyl]-2-methylamino-propionamide Combination in A375

Figure 18:
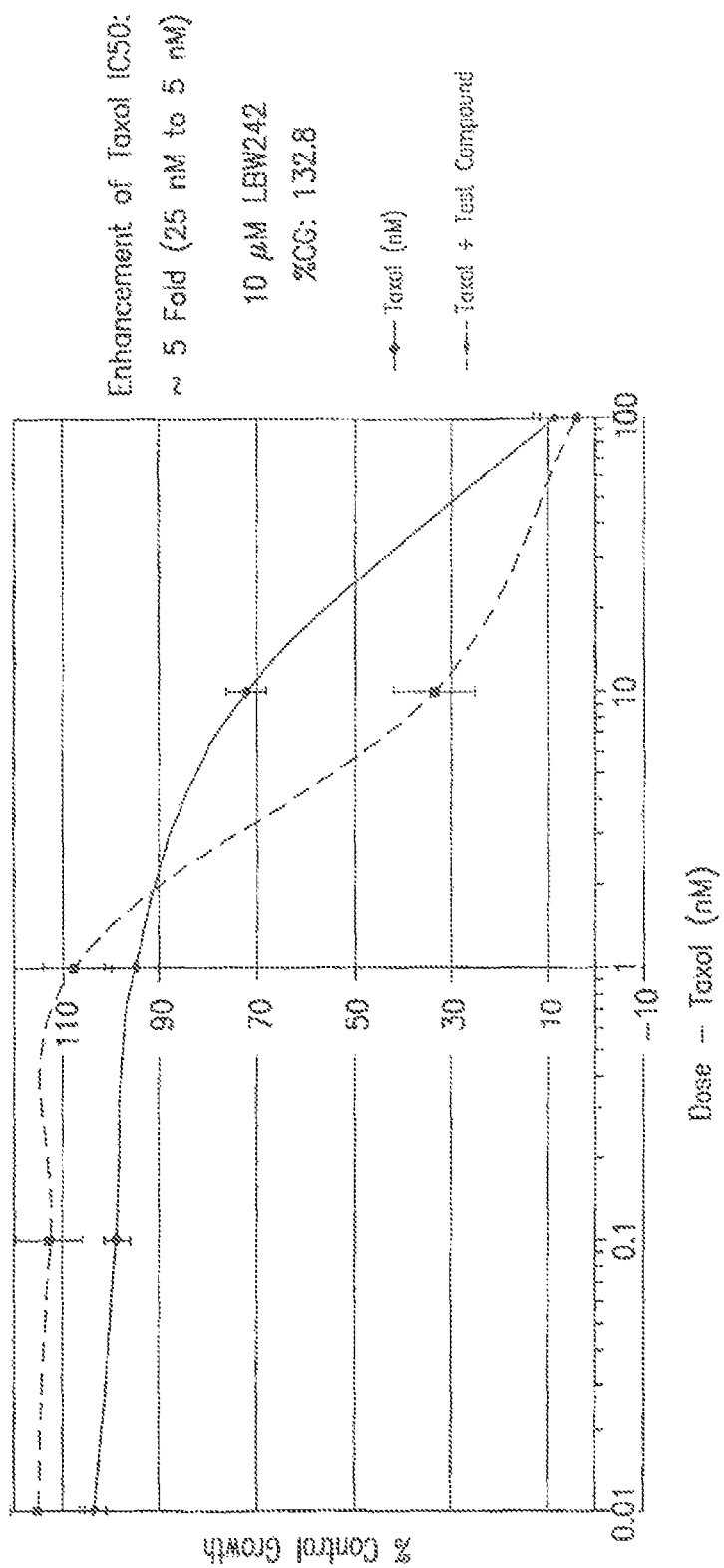
FIG. 18 illustrates Taxol+10 uM N-[1-Cyclohexyl-2-oxo-2-(6-phenethyl-octahydro-pyrrolo[2,3-c]pyridin-1-yl)-ethyl]-2-methylamino-propionamide Combination in A375.

FIG. 18 Taxol+10 uM N-[1-Cyclohexyl-2-oxo-2-(6-phenethyl-octahydro-pyrrolo[2,3-c]pyridin-1-yl)-ethyl]-2-methylamino-propionamide Combination in A375

Figure 19:
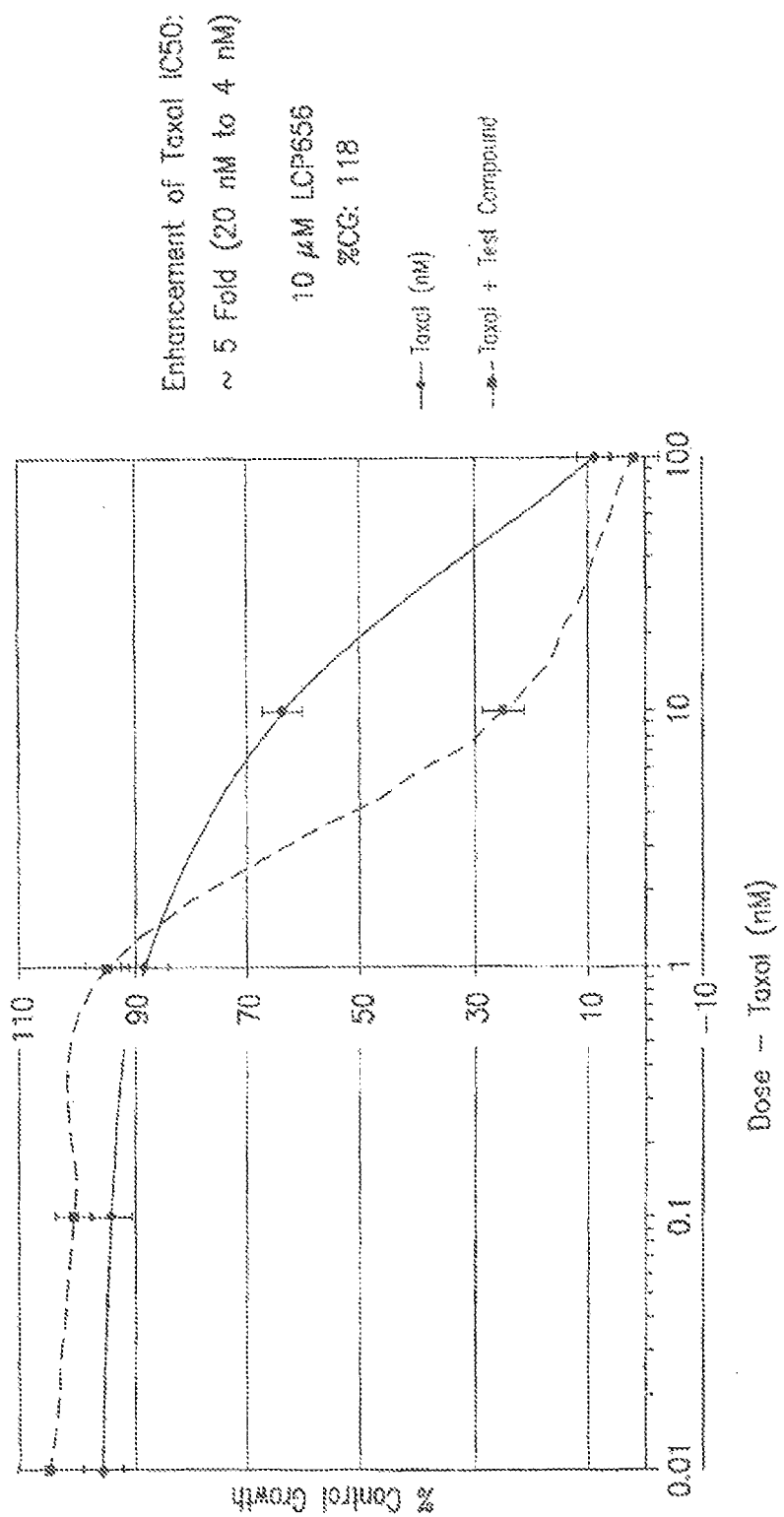
FIG. 19 illustrates Taxol+10 uM N-(1-Cyclohexyl-2-{2-[5-(4-fluoro-phenoxy)-pyridin-3-yl]-pyrrolidin-1-yl}-2-oxo-ethyl)-2-methylamino-propionamide Combination in A375.

FIG. 19 Taxol+10 uM N-(1-Cyclohexyl-2-{2-[5-(4-fluoro-phenoxy)-pyridin-3-yl]-pyrrolidin-1-yl}-2-oxo-ethyl)-2-methylamino-propionamide Combination in A375

Figure 20:
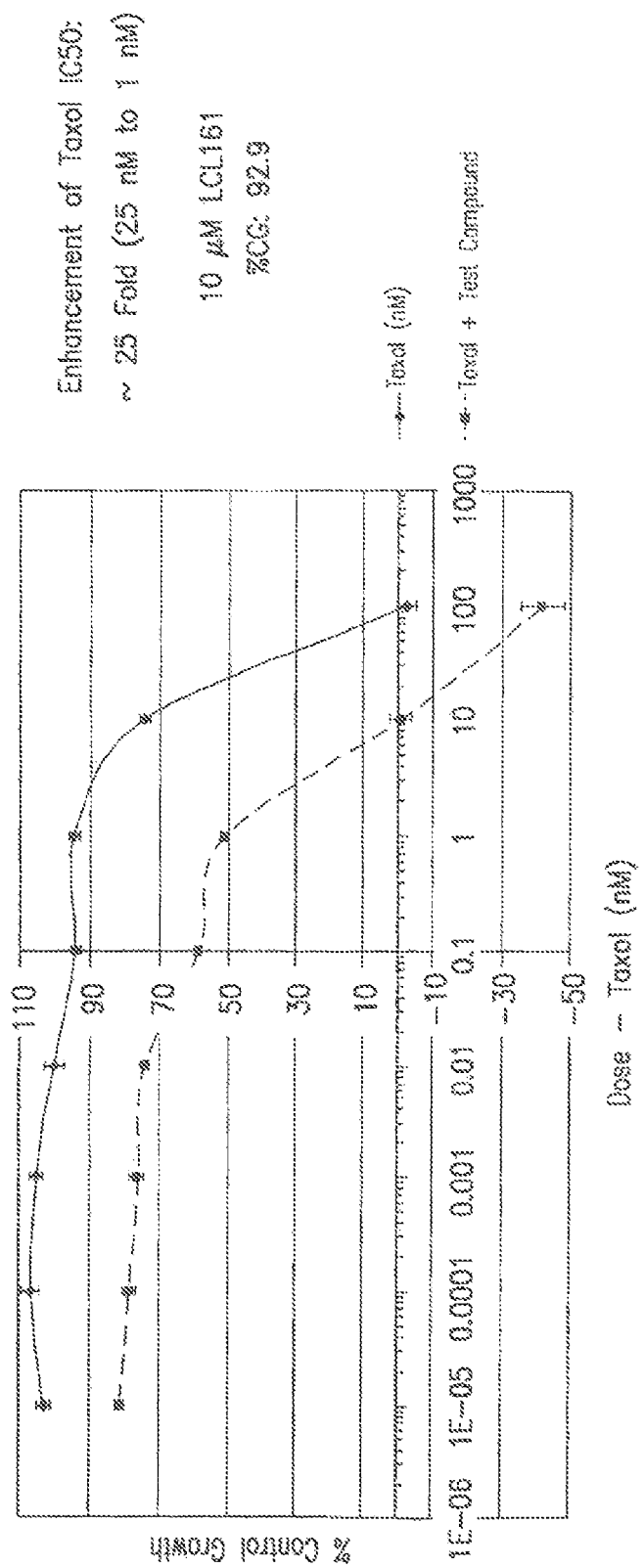
FIG. 20 illustrates Taxol+10 uM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in NCI-H2030.

Lung Tumor Cell Lines:

FIG. 20 Taxol+10 uM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in NCI-H2030

Figure 21:
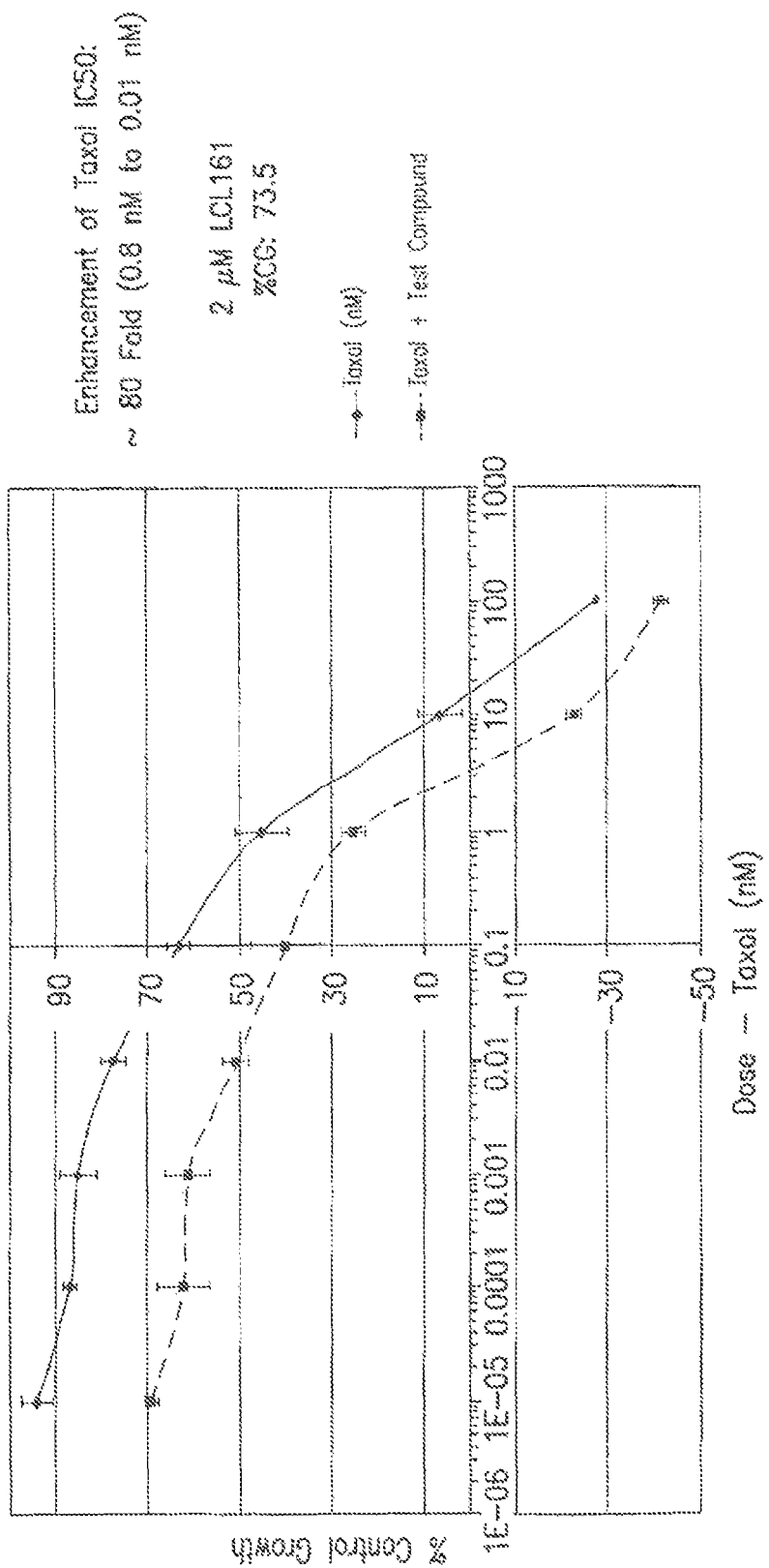
FIG. 21 illustrates Taxol+2 uM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in NCI-H23.

FIG. 21 Taxol+2 uM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in NCI-H23

Figure 22:
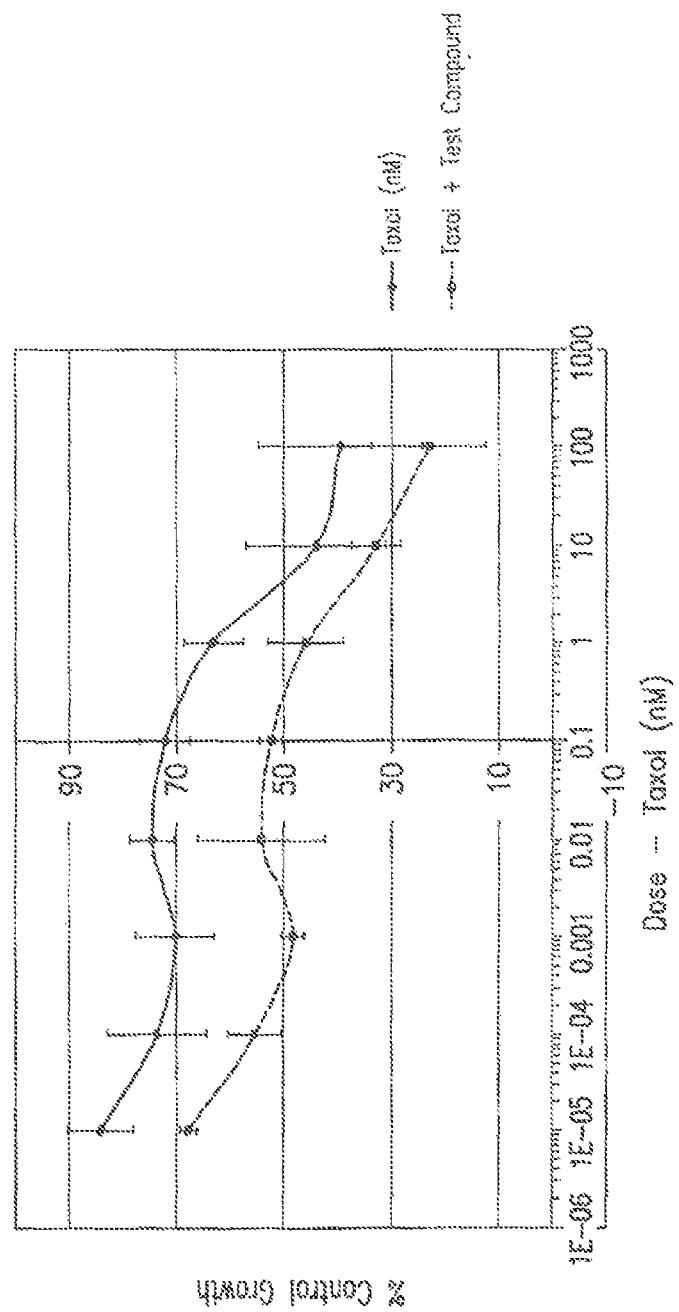
FIG. 22 illustrates Taxol+0.5 uM N-[1-Cyclohexyl-2-oxo-2-(6-phenethyl-octahydro-pyrrolo[2,3-c]pyridin-1-yl)-ethyl]-2-methylamino-propionamide Combination in SK-LU-1.

FIG. 22 Taxol+0.5 uM N-[1-Cyclohexyl-2-oxo-2-(6-phenethyl-octahydro-pyrrolo[2,3-c]pyridin-1-yl)-ethyl]-2-methylamino-propionamide Combination in SK-LU-1

Figure 23:
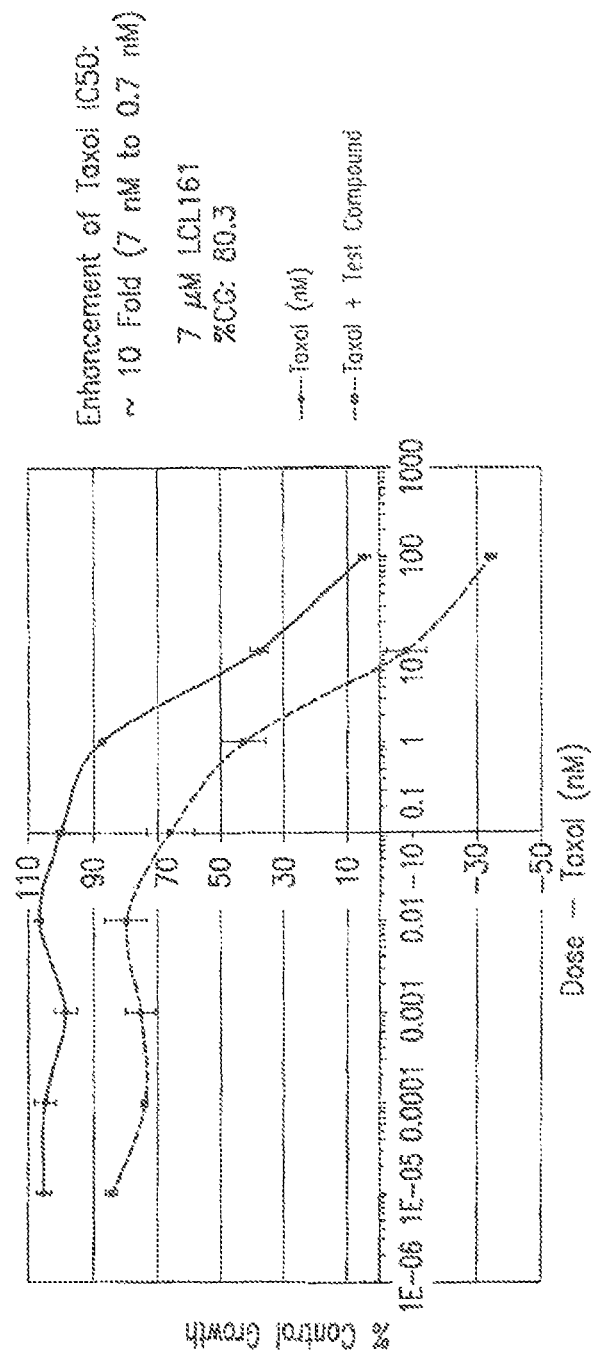
FIG. 23 illustrates Taxol+7 uM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in NCI-H441.

FIG. 23 Taxol+7 uM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in NCI-H441

Figure 24:
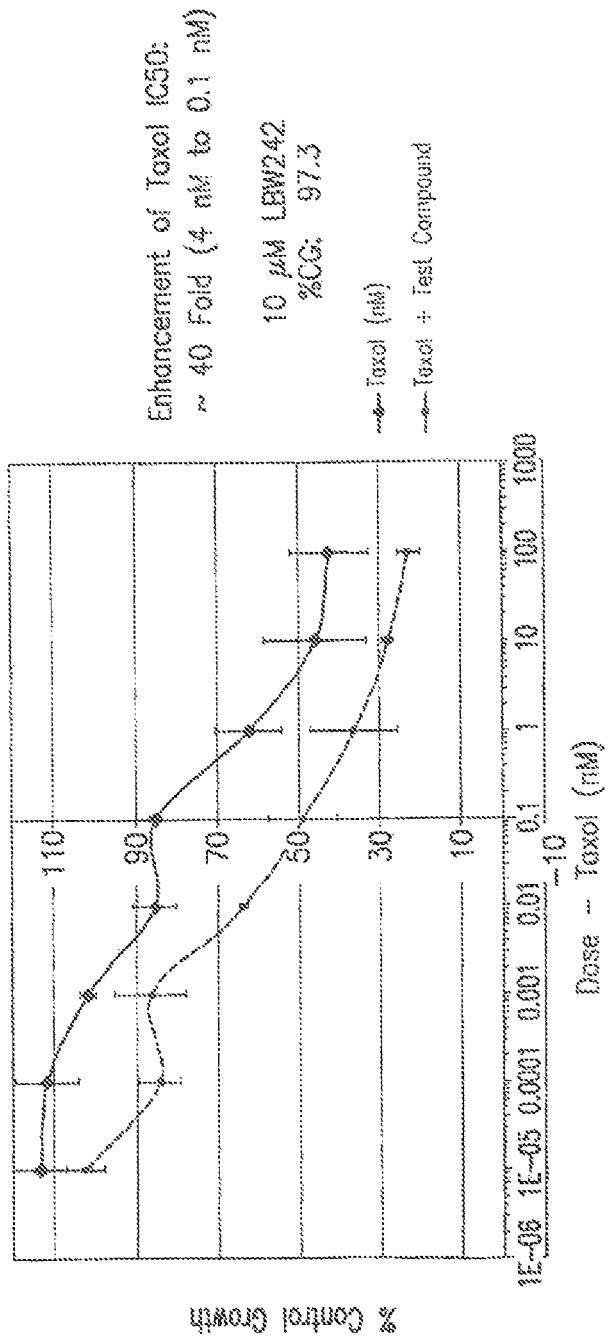
FIG. 24 illustrates Taxol+N-[1-Cyclohexyl-2-oxo-2-(6-phenethyl-octahydro-pyrrolo[2,3-c]pyridin-1-yl)-ethyl]-2-methylamino-propionamide Combination in NCI-H441.

FIG. 24 Taxol+N-[1-Cyclohexyl-2-oxo-2-(6-phenethyl-octahydro-pyrrolo[2,3-c]pyridin-1-yl)-ethyl]-2-methylamino-propionamide Combination in NCI-H441

Figure 25:
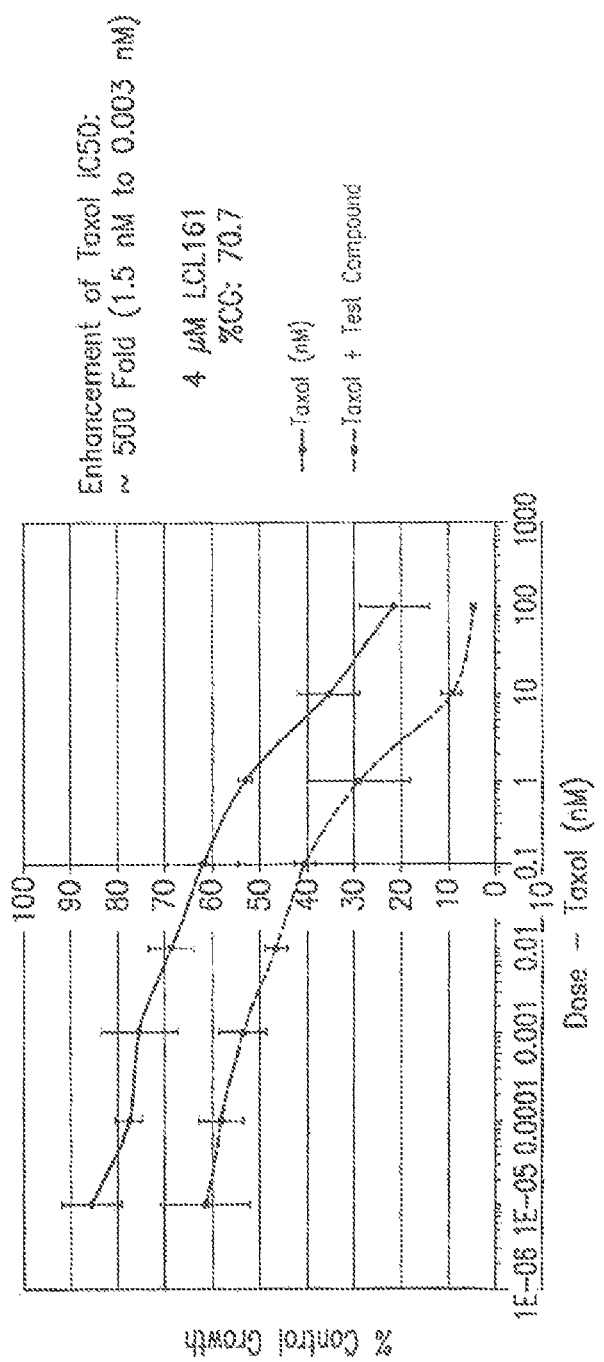
FIG. 25 illustrates Taxol+4 uM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in A-427.

FIG. 25 Taxol+4 uM N-(1-Cyclohexyl-2-{2-[4-(4-fluoro-benzoyl)-thiazol-2-yl]-pyrrolidin-1-yl}-2-oxo-ethyl)-2-methylamino-propionamide Combination in A-427

Figure 26:
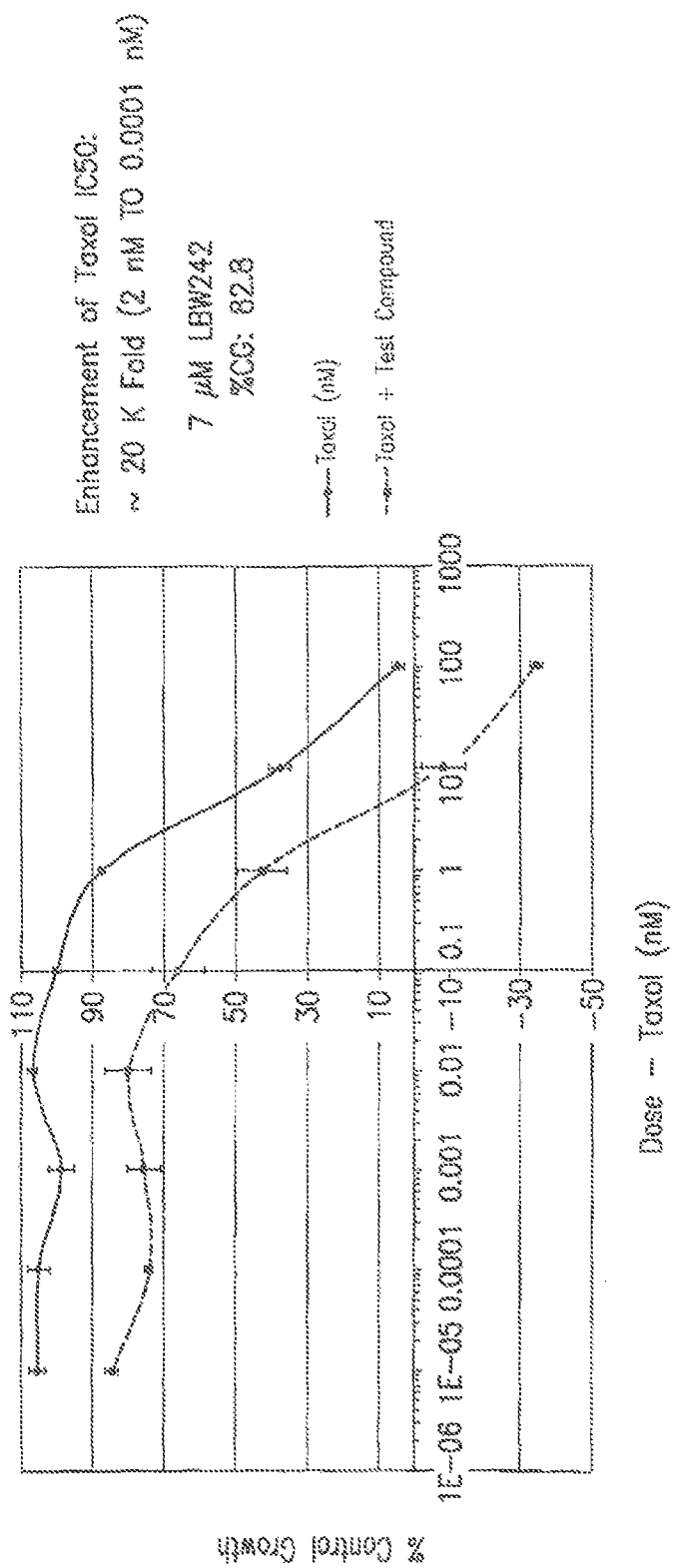
FIG. 26 illustrates Taxol+10 uM N-[1-Cyclohexyl-2-oxo-2-(6-phenethyl-octahydro-pyrrolo[2,3-c]pyridin-1-yl)-ethyl]-2-methylamino-propionamide Combination in A-427.

FIG. 26 Taxol+10 uM N-[1-Cyclohexyl-2-oxo-2-(6-phenethyl-octahydro-pyrrolo[2,3-c]pyridin-1-yl)-ethyl]-2-methylamino-propionamide Combination in A-427

We claim:

1. A pharmaceutical combination comprising co-administration of
    (a) at least one taxane, and
    (b) N-(1-Cyclohexyl-2-{2-[4-(4-fluoro-benzoyl)-thiazol-2-yl]-pyrrolidin-1-yl}-2-oxo-ethyl)-2-methylamino-propionamide or a pharmaceutically acceptable salt thereof.

2. The pharmaceutical combination of claim 1, wherein the taxane is selected from the group consisting of paclitaxel, docetaxel, vinorelbine, the epothilones and combinations thereof.

3. The pharmaceutical combination of claim 2, wherein the taxane is paclitaxel.

4. The pharmaceutical combination of claim 2, wherein the taxane is the combination of paclitaxel and docitaxel.

5. The pharmaceutical combination of claim 1 wherein the taxane and N-(1-Cyclohexyl-2-{2-[4-(4-fluoro-benzoyl)-thiazol-2-yl]-pyrrolidin-1-yl}-2-oxo-ethyl)-2-methylamino-propionamide are administered simultaneously or sequentially in any order.

6. The pharmaceutical combination of claim 1 wherein the taxane and N-(1-Cyclohexyl-2-{2-[4-(4-fluoro-benzoyl)-thiazol-2-yl]-pyrrolidin-1-yl}-2-oxo-ethyl)-2-methylamino-propionamide are administered simultaneously, separately or sequentially in any order.

* * * * *